US005855216A

United States Patent [19]
Robinson

[11] Patent Number: 5,855,216
[45] Date of Patent: Jan. 5, 1999

[54] DENTAL FLOSSING DEVICE

[76] Inventor: Dane Q. Robinson, 6015 E. Quartz Mountain Rd., Paradise Valley, Ariz. 85253

[21] Appl. No.: 948,405

[22] Filed: Oct. 9, 1997

[51] Int. Cl.$^6$ .................................................. A61C 15/00
[52] U.S. Cl. .......................... 132/322; 423/118; 423/143
[58] Field of Search .................................. 132/322, 321, 132/329, 328; 433/82, 118, 125, 127, 142, 143, 165, 166; 601/139, 141, 142

[56] References Cited

U.S. PATENT DOCUMENTS

| Re. 30,536 | 3/1981 | Perdreaux, Jr. ........................... 433/86 |
| 2,931,371 | 4/1960 | Petitta ....................................... 132/89 |
| 3,472,045 | 10/1969 | Nelson et al. ................................. 64/4 |
| 3,552,022 | 1/1971 | Axelsson .................................... 32/58 |
| 3,559,292 | 2/1971 | Weissman .................................. 33/169 |
| 3,563,233 | 2/1971 | Bodine ...................................... 128/36 |
| 3,660,902 | 5/1972 | Axelsson .................................... 32/58 |
| 3,672,378 | 6/1972 | Silverman .................................. 132/93 |
| 3,809,977 | 5/1974 | Balamuth et al. ....................... 318/116 |
| 3,902,510 | 9/1975 | Roth ...................................... 132/92 A |
| 3,967,617 | 7/1976 | Krolik ..................................... 128/36 |
| 4,004,344 | 1/1977 | Gold et al. ................................. 32/27 |
| 4,019,522 | 4/1977 | Elbreder ................................... 132/90 |
| 4,048,723 | 9/1977 | Thorup ...................................... 32/40 |
| 4,205,665 | 6/1980 | Baccialon .............................. 128/62 A |
| 4,235,253 | 11/1980 | Moore ................................... 132/92 R |
| 4,319,377 | 3/1982 | Tarrson et al. ........................... 15/111 |
| 4,319,595 | 3/1982 | Ulrich .................................. 132/92 R |
| 4,326,547 | 4/1982 | Verplank ................................. 132/89 |
| 4,347,839 | 9/1982 | Youngclaus, Jr. ...................... 128/62 A |
| 4,397,327 | 8/1983 | Hadary ..................................... 132/89 |
| 4,577,649 | 3/1986 | Shimenkov ............................... 1332/93 |
| 4,608,019 | 8/1986 | Kumabe et al. ......................... 433/118 |
| 4,634,376 | 1/1987 | Mossle et al. ............................ 433/29 |
| 4,791,940 | 12/1988 | Hirschfeld et al. ..................... 128/776 |
| 4,820,154 | 4/1989 | Romhild et al. ........................ 433/128 |
| 4,832,063 | 5/1989 | Smole ..................................... 132/329 |
| 4,913,133 | 4/1990 | Tichy .................................... 128/62 A |
| 4,922,936 | 5/1990 | Buzzi et al. ............................ 132/321 |
| 4,995,403 | 2/1991 | Beckman et al. ...................... 128/776 |
| 5,000,684 | 3/1991 | Odrich ................................... 433/125 |
| 5,002,487 | 3/1991 | Tichy ..................................... 433/122 |
| 5,050,625 | 9/1991 | Siekmann .............................. 132/323 |
| 5,069,621 | 12/1991 | Paradis .................................. 433/147 |
| 5,071,348 | 12/1991 | Woog .................................... 433/118 |
| 5,100,321 | 3/1992 | Coss et al. ............................. 433/118 |
| 5,123,841 | 6/1992 | Millner ................................... 433/125 |
| 5,125,837 | 6/1992 | Warrin et al. ............................ 433/98 |
| 5,138,733 | 8/1992 | Bock .................................... 15/22.1 |
| 5,224,500 | 7/1993 | Stella .................................... 132/322 |
| 5,236,358 | 8/1993 | Sieffert .................................. 433/119 |
| 5,247,716 | 9/1993 | Bock .................................... 15/22.1 |
| 5,293,886 | 3/1994 | Czapor .................................. 132/329 |
| 5,369,831 | 12/1994 | Bock .................................... 15/22.1 |
| 5,419,703 | 5/1995 | Warrin et al. .......................... 433/216 |
| 5,546,624 | 8/1996 | Bock .................................... 15/22.1 |
| 5,573,020 | 11/1996 | Robinson .............................. 132/322 |
| 5,787,908 | 8/1998 | Robinson .............................. 132/322 |

FOREIGN PATENT DOCUMENTS

| 0 354 352 | 2/1990 | European Pat. Off. . |
| 42 26 659 | 2/1994 | Germany . |
| 43 09 078 | 3/1994 | Germany . |
| WO 94/04093 | 3/1994 | WIPO . |
| WO 95/02375 | 1/1995 | WIPO . |

*Primary Examiner*—Gene Mancene
*Assistant Examiner*—Pedro Philogene
*Attorney, Agent, or Firm*—Seed and Berry LLP

[57] ABSTRACT

An apparatus for cleaning the surface of teeth in a human mouth having a flexible, resilient central flossing filament and a plurality of flexible side flossing filaments fixedly attached to a central filament intermediate portion. The central filament intermediate and free end portions, with the side flossing filaments attached thereto, are sized to be received between adjacent teeth without traversing any contact areas between the adjacent teeth from at least the front of the mouth. The central filament has sufficient flexibility and resiliency to effect a first flossing action between the adjacent teeth by imparting a first flossing motion to the central filament, and the side filaments have sufficient flexibility to effect a second flossing action between the adjacent teeth and at the forward and rearward surfaces thereof to impart a second flossing motion to the side filaments. An electric motor is coupled to the central filament base portion to provide a rotational or an oscillatory drive to the central filament base portion to impart the first and second flossing motions. The central filament has greater resiliency than the side filaments. The side filaments have greater flexibility than the central filament, and are sufficiently flexible to bend back adjacent the central filament upon insertion between the adjacent teeth. Upon a drive force being applied thereto through the central filament the side filaments whip or flail about, and in one embodiment are rotated to spin about the longitudinal driven axis of the central filament.

122 Claims, 7 Drawing Sheets

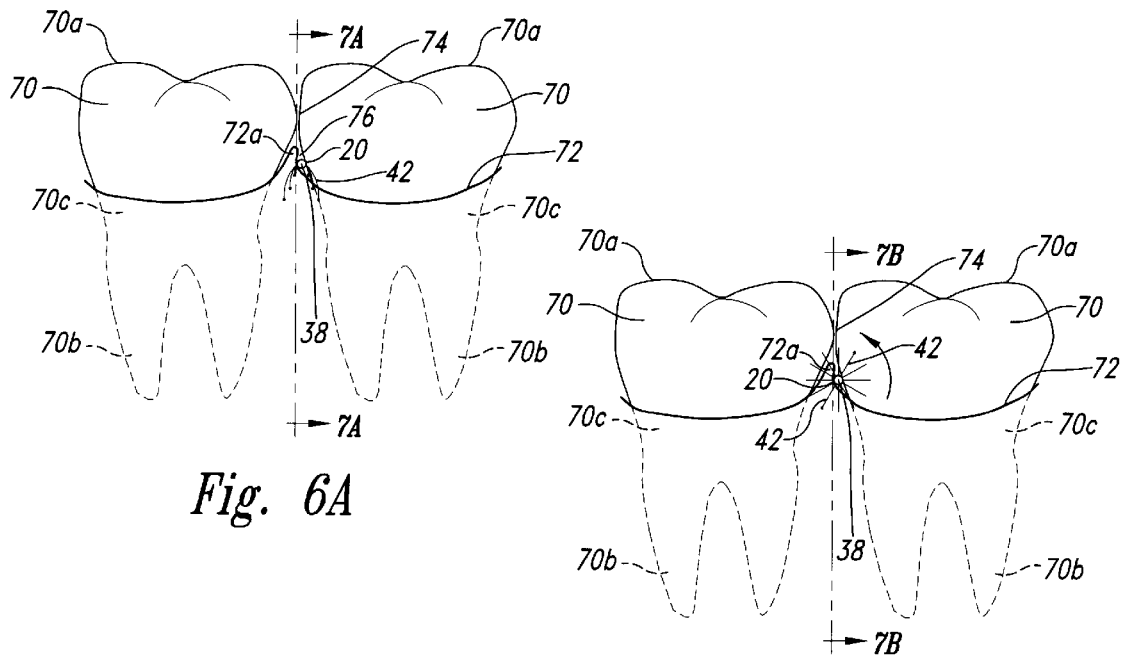
Fig. 6A
Fig. 6B
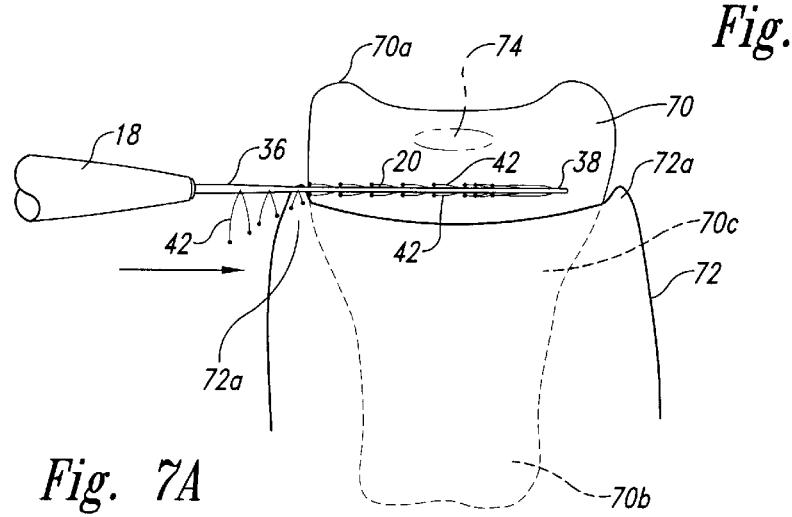
Fig. 7A
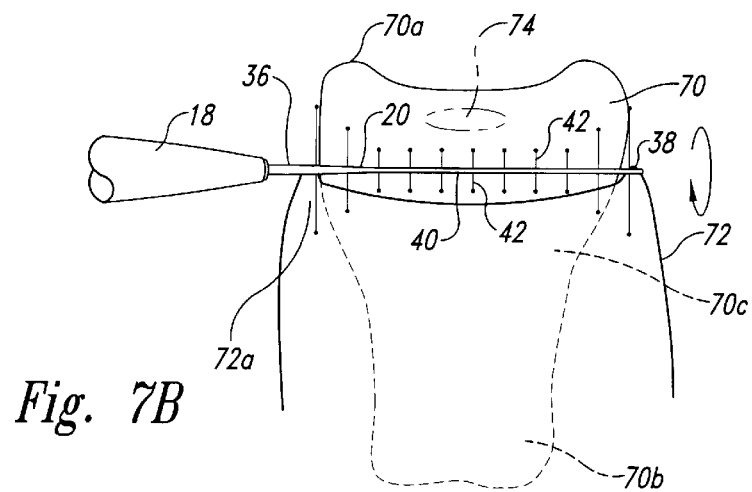
Fig. 7B

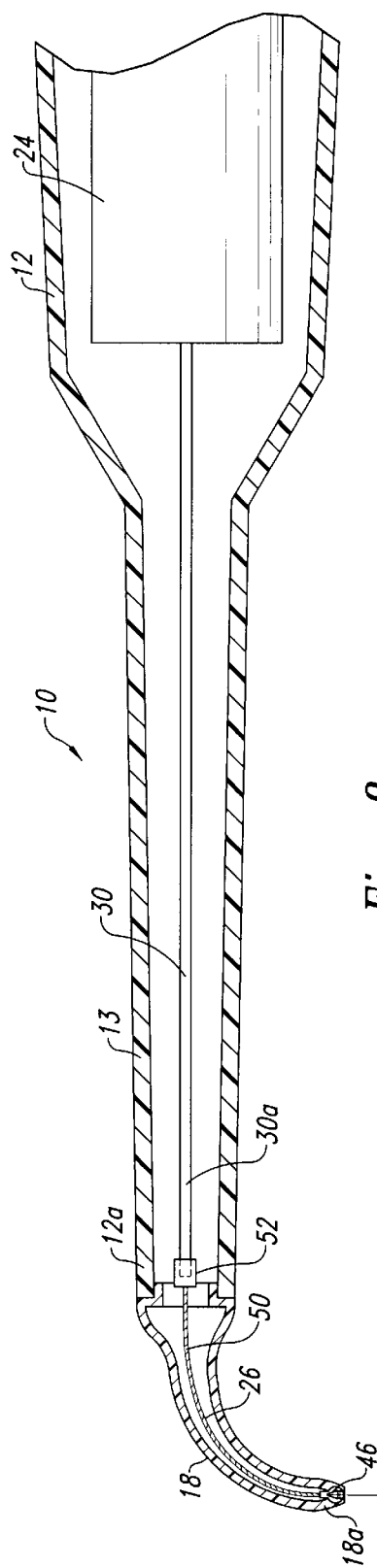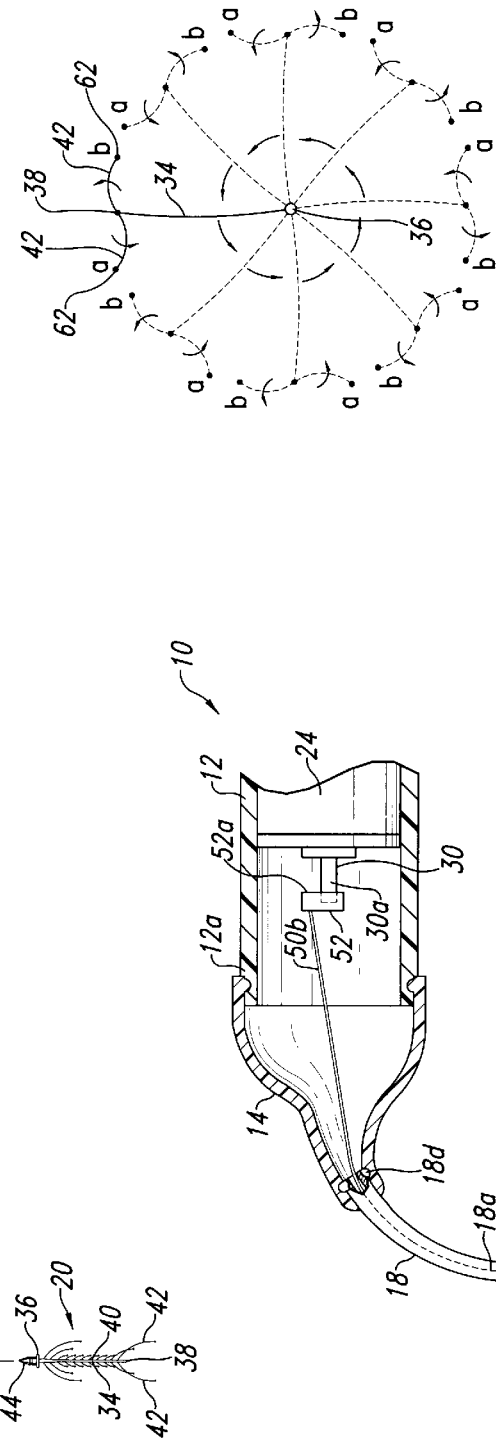

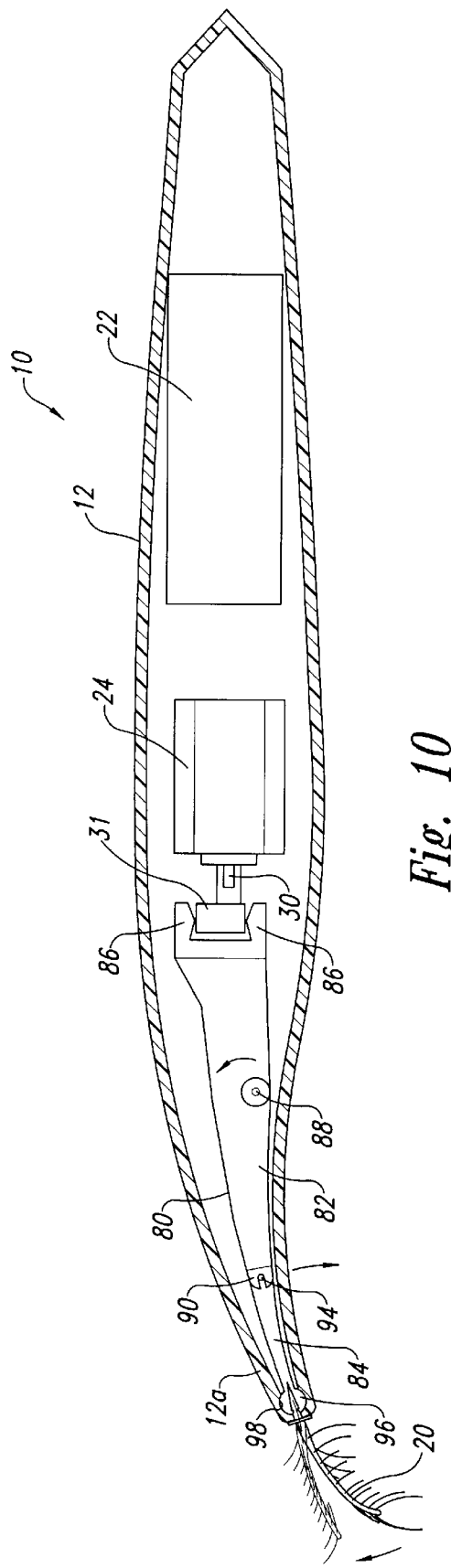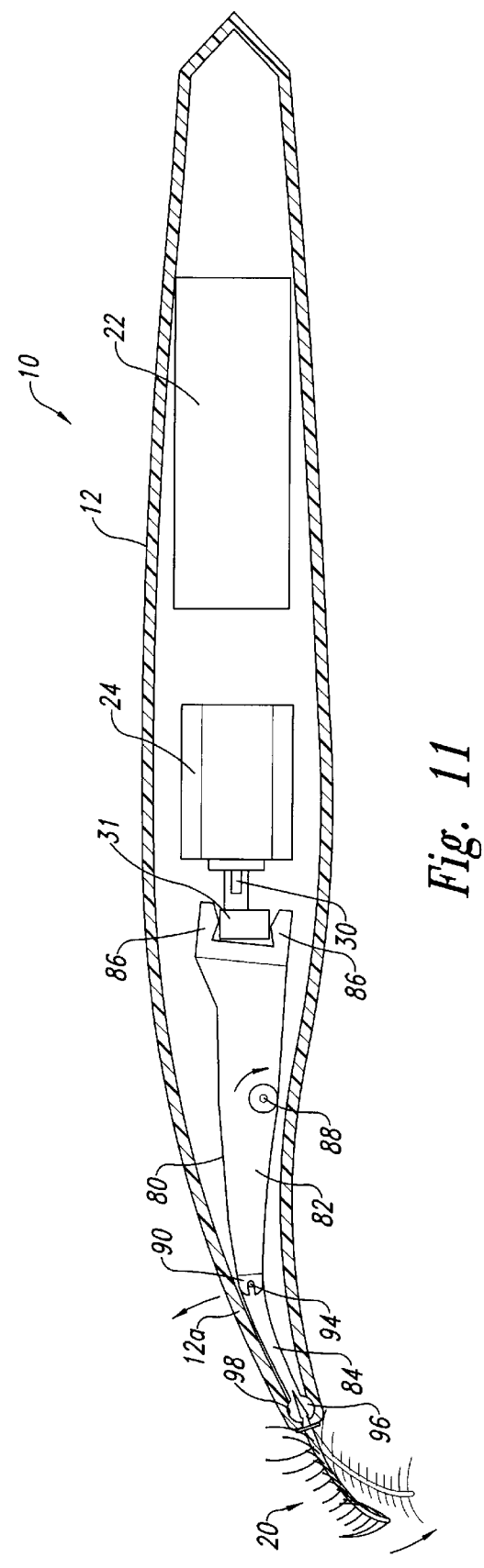

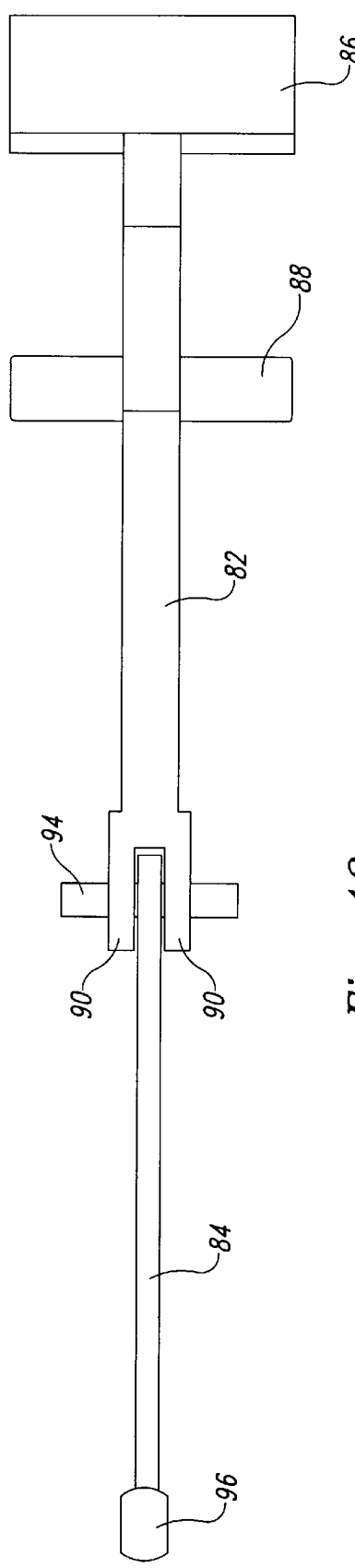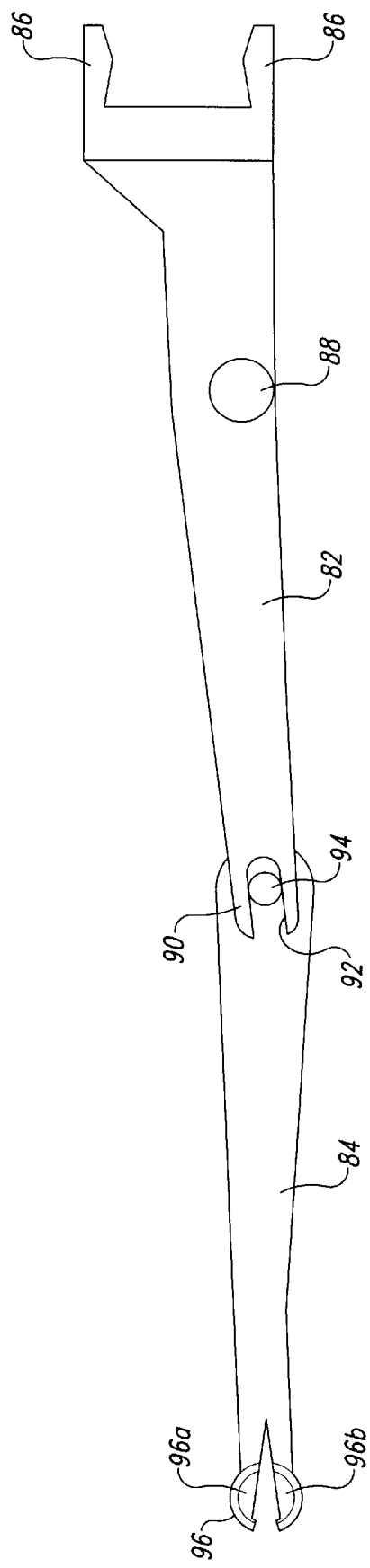

DENTAL FLOSSING DEVICE

TECHNICAL FIELD

This invention generally relates to dental devices and, more specifically, to a hand held electromechanical dental flossing device using a flossing filament.

BACKGROUND OF THE INVENTION

Various types of dental devices and methods exist for the cleaning of teeth as well as for the massaging of the gum tissue. U.S. Pat. No. Re. 30,536, "Ultrasonic Device and Method," issued on Mar. 3, 1981, shows an apparatus which utilizes an ultrasonically driven head in conjunction with a spray of liquid or slurry containing abrasive material to operate as a cutting or cleaning tool in dental operations. U.S. Pat. No. 4,913,133, "Hand Held Periodontic Tool," issued on Apr. 3, 1990, discloses a hand held periodontic tool which vibrates a flexible tip for use in massaging gum tissue, but which cannot be used for dental flossing. Such prior art devices, however, are typically unable to reach the area between the portion of the tooth located beneath the gum tissue surface and the gum tissue itself (inter-dental papilla). This area was generally cleaned with dental floss.

However, the use of dental floss can be somewhat cumbersome. In many instances there are contact areas between the teeth (i.e., portions of the crowns of the teeth are closely adjacent or touching), typically at the top of the crown. In order for floss to be received between the teeth, it is generally necessary for the floss to be forced between the teeth from above, and must pass through any contact area. However, such contact areas often do not provide adequate space to permit passage of the floss. This tends to result in the floss shredding or breaking rather than passing between the teeth. In such instances, some manner of threading device must be employed.

Devices which dispose a strand of floss between rigid arms of a forked or "U" shaped tip to facilitate flossing are available. Electrical flossing devices which reciprocate such a tip are also known, such as described in U.S. Pat. No. 4,235,253, "Electric Dental Flosser" issued Nov. 25, 1980, to D. A. Moore.

A hand held, electrically powered flossing device which solves many of the above-noted problems is shown in applicant's own recently issued U.S. Pat. No. 5,573,020, "Dental Flossing Device and Method Therefor," issued Nov. 12, 1996. The device utilizes a flexible, resilient non-abrasive filament which is supplied with at least one of a translational or a rotational drive force to impart a flossing motion to an intermediate portion of the flossing filament.

While the device effectively and efficiently cleans or flosses the area between the teeth, and also the area between the inter-dental papilla and the interproximal surface of the tooth, it is desirable to provide an alternative dental flossing device using a flossing filament with increased effectiveness and efficiency.

SUMMARY OF THE INVENTION

The present invention provides an improved electro-mechanical dental flossing device and method therefor which effectively and efficiently provides a flossing action both between and around teeth as well as providing a flossing action between the portion of the tooth that is beneath the gum tissue surface adjacent to the inter-dental papilla.

The present invention resides in a flossing member for cleaning the surfaces of teeth in a human mouth including an elongated central member and a plurality of flexible side flossing filaments attached thereto. In an illustrated embodiment of the invention the central member is a flexible, resilient central flossing filament. In the illustrated embodiment the flossing member is incorporated into an apparatus which further includes a motive source and a coupling connecting the motive source to the central member filament to impart flossing motion to the side flossing filaments and preferably also to the central flossing filament.

At least an intermediate portion of the central member, with the side flossing filaments attached thereto, are sized to be received in the sulcus between a tooth of the adjacent teeth and the adjacent inter-dental papilla portion of the gum for effecting the flossing action therein. In the illustrated embodiments the coupling applies a moving force to the central member with at least one of a rotational and a translational component to move the central member and thereby impart the flossing motion to the side flossing filaments. A moving force applied to the central member with a rotational component moves the central member intermediate portion along a generally conical path of travel to produce the flossing motion of the side flossing filaments. A rotational output drive of the motive source may be translated into an oscillatory drive supplied to the central member to produce the flossing motion of the side flossing filaments.

In general, the motive source provides a drive through the coupling which converts into a moving force applied to the central member which moves the central member along a path of travel substantially out of alignment with the central member when at rest to effect the flossing action of the side flossing filaments. Rotation of the central member is transmitted to the side flossing filaments to rotate the side flossing filaments about a driven longitudinal axis of the central member as the central member rotates. In an illustrated embodiment at least one of the side flossing filaments has a sufficient length and is attached to the central member intermediate portion at a location to be positioned to engage a forward surface of the adjacent teeth, and at least one of the side flossing filaments has a sufficient length and is attached to the central member intermediate portion at a location to be positioned to engage a rearward surface of the adjacent teeth when the central member intermediate portion is received between the adjacent teeth.

The central member intermediate portion has an average transverse dimension of between 0.012 to 0.030 inches. The side filament intermediate portions have a maximum average transverse dimension of between 0.002 to 0.008 inches. The central member intermediate portion has a transverse dimension greater than an average transverse dimension of the side filament intermediate portions. Further, in an illustrated embodiment, the side filament free-end portions have a transverse dimension greater than an average transverse dimension of the side filament intermediate portions. The side filament free-end portions have a maximum average transverse dimension of between 0.004 to 0.010 inches. The average length of the side flossing filaments is between 0.020 to 0.065 inches. In an illustrated embodiment, the side flossing filaments have unequal lengths. In particular, the side flossing filaments have non-uniform lengths varying according to a longitudinal location of the side flossing filaments along the central member intermediate portion. The side flossing filament at the end locations have a length greater than 0.020 inches, preferably 0.045 to 0.065 inches. The side flossing filaments are spaced along the central member intermediate portion by between 0.030 to 0.050 inches.

The side filament intermediate portions are sufficiently flexible to freely bend toward the central member intermediate portion during insertion thereof between the adjacent teeth. Further, the side filament intermediate portions are sufficiently flexible to be unable to fully support their own weight without substantial bending. The side filament intermediate portions have a greater flexibility than the central member intermediate portion, but the central member intermediate portion has a greater resiliency than the side filament intermediate portions. Preferably, the side flossing filaments and the central member are non-abrasive. Further, the side flossing filaments are arranged along the central member intermediate portion in pairs, extending in different directions. In the illustrated embodiment, the side flossing filaments of the pairs extend outward from the central member intermediate portion in opposing directions, preferably transverse to the central member intermediate portion. The side flossing filaments and the central member are molded as an integral unit from a plastic.

The invention further includes a method for cleaning the surfaces of teeth in a human mouth using the foregoing flossing member. The method includes providing a motive source, providing a flexible, resilient central flossing filament, and providing a plurality of flexible side flossing filaments. The central flossing filament and the side flossing filaments are constructed as described above. The method further includes positioning the central filament intermediate portion and free-end portions, with the side flossing filaments attached thereto, between adjacent teeth without traversing any contact areas between the adjacent teeth from the front of the mouth. The method also includes the step of positioning at least the central filament intermediate portion and at least one of the side flossing filaments in the sulcus between a tooth and the adjacent inter-dental papilla portion of the gum for effecting the first and second flossing actions therein. The method farther includes driving the central flossing filament and the side flossing filaments with the motive source to impart the first and second flossing motions to the central filament intermediate portion and the side flossing filaments, respectively.

Other features and advantages of the invention will become apparent from the following detailed description, taken in conjunction with the accompanying drawings.

BRIEF DESCRIPTION OF THE DRAWINGS

FIG. 6A is an end view of the flossing member of FIG. 2A shown from within the mouth inserted between the two teeth without the flossing member drive force being supplied.

FIG. 6B is an end view of the flossing member of FIG. 2A shown from within the mouth inserted between the two teeth with the flossing member having a drive force supplied to rotate the flossing member.

FIG. 7A is a side elevational view taken along the line 7A—7A of FIG. 6A.

FIG. 7B is a side elevational view taken along the line 7B—7B of FIG. 6B.

FIG. 8 is a fragmentary, longitudinal cross-sectional view of a first alternative embodiment of the flossing device of FIG. 1.

FIG. 9A is a fragmentary, longitudinal cross-sectional view of a second alternative embodiment of the flossing device of FIG. 1 which supplies translational and rotational drive force to the flossing member.

FIG. 9B is a schematic end view of the flossing member used with the second alternative embodiment of FIG. 9A shown in various positions when having a translational and rotational drive force supplied thereto.

FIG. 10 is a longitudinal cross-sectional view of a third alternative embodiment of the flossing device of FIG. 1 which supplies a translational drive force to the flossing member using a translation arm.

FIG. 11 is a longitudinal cross-sectional view of the flossing device of FIG. 10 with the translation arm moved to another position.

FIG. 12 is an enlarged top plan view of the translation arm of FIG. 10.

FIG. 13 is an enlarged side elevational view of the translation arm of FIG. 10.

DETAILED DESCRIPTION OF THE INVENTION

Figure 3:
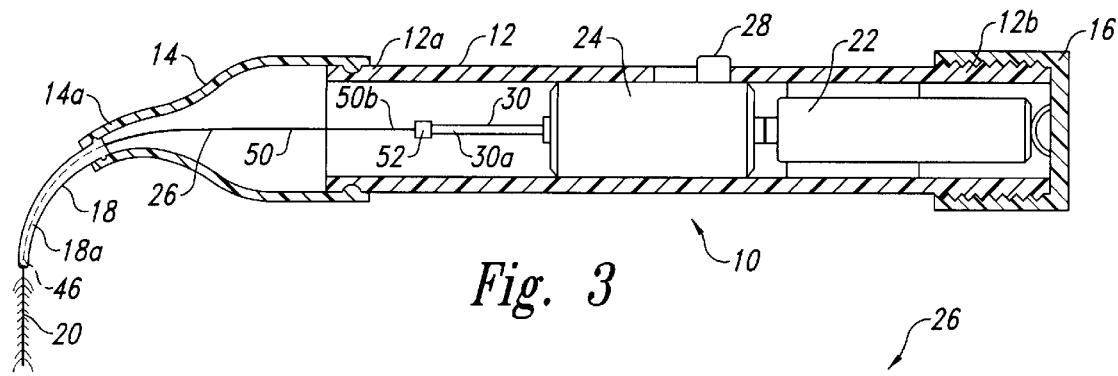
FIG. 3 is an enlarged, longitudinal cross-sectional view of the flossing device of FIG. 1 taken along the line 3—3 of FIG. 1.

As shown in the drawings for purposes of illustration, the present invention is embodied in an electromechanical dental flossing device, indicated generally by reference numeral 10, used to floss teeth. The flossing device 10 shown in FIGS. 1 and 3 includes an elongated, generally cylindrical case 12 sized to be hand held and serving as a handle, a generally conical resilient tip or boot 14 removably snap fit over a open forward end 12*a* of the case, a threaded end cap 16 removably threaded to a threaded rearward end 12*b* of the case, and a resilient insert or coupler support 18 removably snap fit within a forward end 14a of the boot. An elongated flossing member 20 extends outward through a forward end portion 18a of the coupler support 18 and beyond the coupler support. As illustrated in FIG. 3, within the case 12 the flossing device 10 includes a power source 22 such as a battery, an electric motor 24 and a coupler 26 coupling the flossing member 20 to the motor. The coupler support 18 and the coupler 26 serve as a coupling to releasably connect the flossing member 20 to the case 12 and to the motor 24. The flossing device 10 may also be powered by other sources of power such as wall voltage using a power cord (not shown).

A manually operated electrical control switch 28 is mounted to the case 12 and extends inward through a sidewall of the case and is electrically connected to selectively apply power from the power source 22 to the motor 24 to energize the motor and cause rotation of an output shaft 30 of the motor. The resulting rotation of the shaft 30 supplies a rotational drive force to rotate the flossing member 20.

Figure 1:
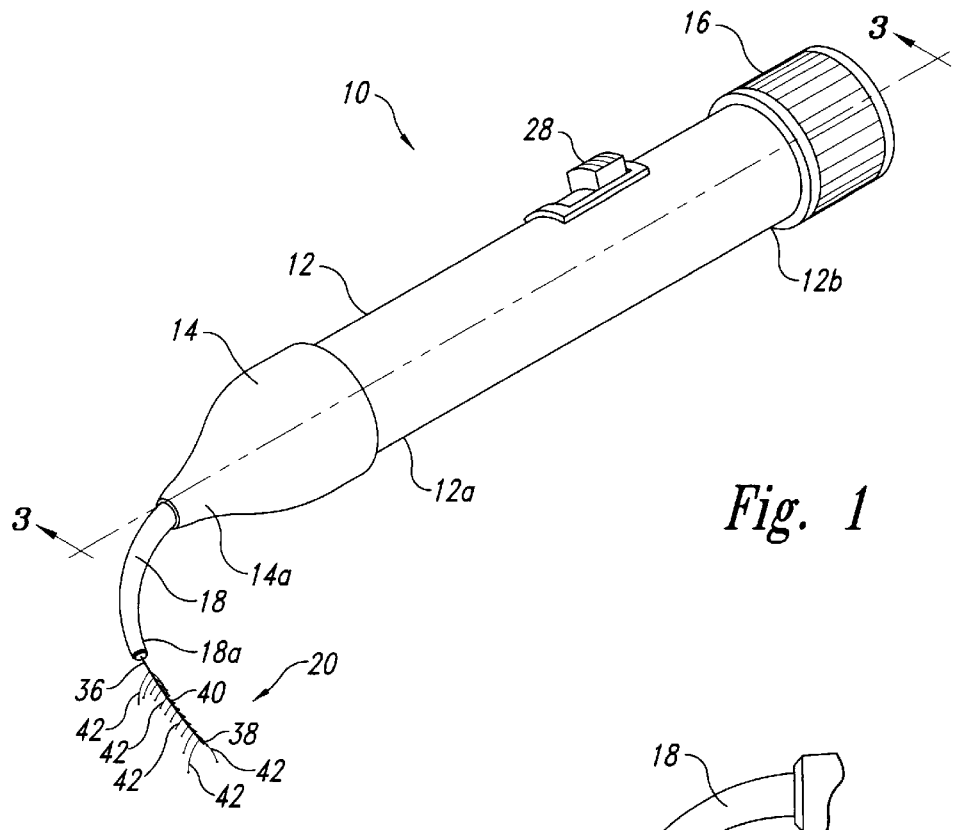
FIG. 1 is a perspective view of a first embodiment of a flossing device in accordance with the present invention using a flossing member with a central flossing filament and side flossing filaments.
Figure 2A:
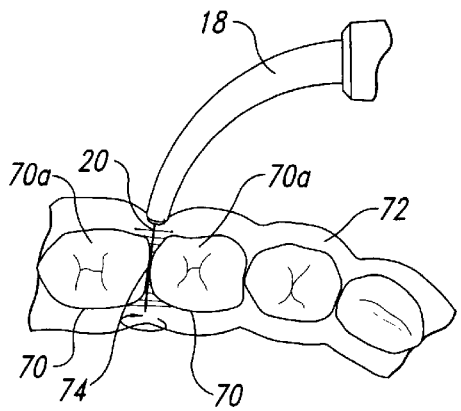
FIG. 2A is a bottom view showing the flossing member of the flossing device of FIG. 1 flossing the area between two teeth.
Figure 2B:
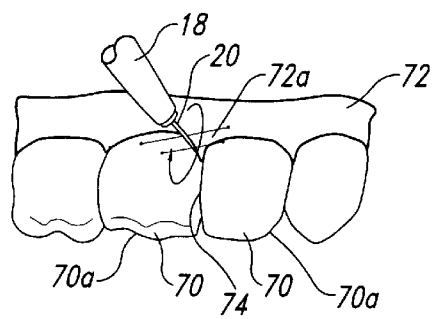
FIG. 2B is a front perspective view of the teeth of FIG. 2A showing the flossing member of the flossing device of FIG. 1 flossing the area between a portion of a tooth that is beneath the gum tissue surface and the gum tissue itself.
Figure 5A:
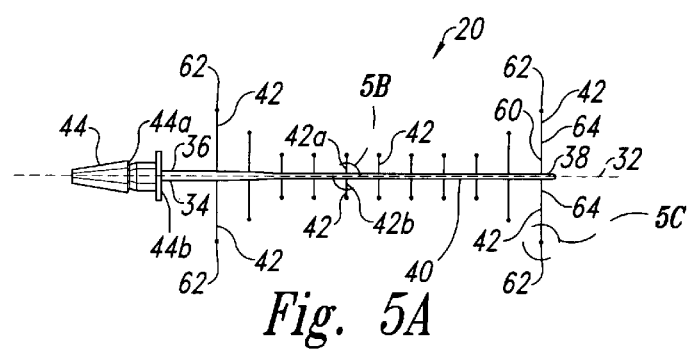
FIG. 5A is an enlarged side view of the flossing member of the flossing device of FIG. 1 shown detached from the attachment head.

The flossing member 20 has a stationary longitudinal axis, shown in FIG. 5A by broken line 32, extending along the length and a longitudinal extension line of the flossing member when the flossing filament is not driven to move by the motor 24. This stationary longitudinal axis 32 may extend along a curved or straight line depending on the curve of the flossing filament 20 when not being driven. When supplied with a drive force having a rotational component, the flossing member 20 is driven at least initially to rotate about its stationary longitudinal axis 32. However, if the flossing filament 20 has sufficient flexibility, resiliency and length, the rotation tends to cause the flossing member 20 to bend outward under the driving rotational force applied and the centrifugal force that results, and to whip or flail about moving along a path of travel with a plurality of successive positions substantially bent out of alignment with the stationary longitudinal axis 32 and with a component of motion out of alignment with the stationary longitudinal axis. While this off-axis whipping or flailing action occurs, the flossing member 20 continues to be driven to rotate about a rotational or driven longitudinal axis which extends along the length and a longitudinal extension line of the flossing member as it bends, and which is constantly changing with respect to and only occasionally in alignment with the stationary longitudinal axis 32, if at all. In the embodiment of FIG. 1 and the first alternative embodiment of FIG. 8, the drive force supplied by the motor 24 to the flossing member 20 has only a rotational drive component. As will be described below, other illustrated embodiments supply a drive force with both rotational and translational components, or with only a translational component.

As best shown in FIG. 5A, the flossing member 20 includes a flexible and resilient elongated central flossing filament 34 having a base portion 36, a tip or free-end portion 38, and an elongated intermediate portion 40 extending between the free-end portion and the base portion. The flossing member 20 further includes a plurality of side flossing filaments 42 attached to the intermediate portion 40 of the central flossing filament 34. The stationary longitudinal axis 32 and the driven longitudinal axis of the flossing member is generally coaxial with the longitudinal axis of the intermediate portion 40 of the central flossing filament 34.

The tip and intermediate portions 38 and 40 of the central flossing filament 34 are non-abrasive and the intermediate portion has sufficient stiffness to be self-supporting and to support the weight of the side flossing filaments 42. The intermediate portion 40 has sufficient flexibility, resiliency and length so that it will whip or flail about when driven at a sufficiently fast rotational speed and provide a cleaning action resulting from the impact or whacking of the intermediate portion against the inter-proximal tooth surfaces as well as its up and down stroking of the inter-proximal tooth surfaces. As noted above, the driven longitudinal axis of flossing member 20 is rarely in alignment with the stationary longitudinal axis 32. Less whipping or flailing action will result if the intermediate portion 40 is stiffened, and if sufficiently stiff, the driven longitudinal axis will remain substantially in alignment with the stationary longitudinal axis and the cleaning action will be provided almost completely by the side flossing filaments 42, as will be described in greater detail below.

The plurality of side flossing filaments 42 attached to the intermediate portion 40 extend generally transverse thereto. For purposes of illustration, the side flossing filaments 42 are shown in FIG. 5A as if the flossing member 20 is laid on a flat surface with the side flossing filaments arranged in parallel alignment. In actuality, when not being rotatably driven by the motor 24, the side flossing filaments are very limp and do not have sufficient rigidity to fully support their weight without substantial bending. As such, when the flossing member 20 is held stationary in a horizontal position without the side flossing filaments 42 being supported except by their connection to the central flossing filament 34, the side flossing filaments droop as shown in FIG. 5D.

Figure 4:
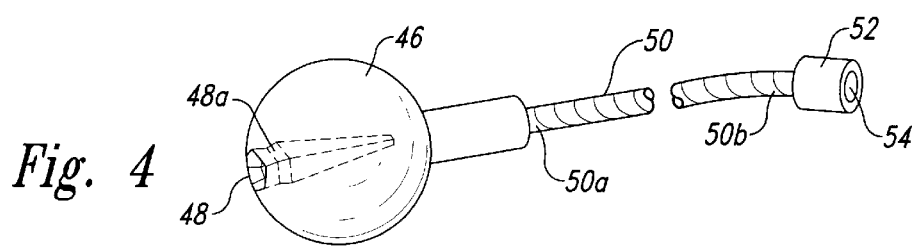
FIG. 4 is an enlarged, fragmentary perspective view of a drive cable and flossing member attachment head used in the flossing device of FIG. 1 shown removed from the device.

The base portion 36 of the central flossing filament 34 includes a connector member 44. As previously stated, the flossing member 20 is coupled to the motor 24 by the coupler 26. As best shown in FIGS. 4 and 5D, the coupler 26 includes a generally spherical attachment head 46 having a socket 48 with a size and five-sided shape to removably receive therein, in a snap fit arrangement, the connector member 44 of the central flossing filament 34. The connector member 44 has a corresponding size and five-sided shape, and is sufficiently compressible and resilient to be pushed into and later removed from the socket 48 of the attachment head 46. When within the socket 48, a shoulder portion 44a on each of the five sides of the connector member 44 frictionally engages a corresponding shoulder portion 48a on each of five sides of the socket 48 to securely but removably hold the connector member in place within the socket 48 and apply a rotational drive force thereto, as will be described below.

The coupler 26 further includes a flexible drive cable 50 having a forward end portion 50a fixedly attached to the attachment head 46 in alignment with a chord of the spherical attachment head passing through the center point of the attachment head (i.e., along a diameter line) so that rotation of the drive cable about its longitudinal axis rotates the attachment head about its center point. The socket 48 of the attachment head 46 is arranged to grasp and hold the base portion 36, and hence the rearward end portion of the intermediate portion 40 adjacent thereto, in coaxial alignment with the forward end portion 50a of the drive cable 50, to transmit the rotation of the drive cable to the central flossing filament 34 in a generally coaxial arrangement. As best shown in FIG. 5D, the spherical attachment head 46 is rotatably and removably retained in a similarly sized and generally spherical socket 18b formed in the forward end portion 18a of the coupler support 18. The spherical socket 18b rotatably retains the attachment head 46 to allow its free spinning or rotation therein when the coupler 26 is rotatably driven by the motor 24.

The drive cable 50 further has a rearward end portion 50b fixedly attached to a shaft connector 52. The shaft connector 52 has a socket 54 sized to snugly and removably receive therein and frictionally engage a forward end portion 30a of the output shaft 30 of the motor 24. The shaft connector 52 holds the rearward end portion 50b of the drive cable 50 in general coaxial alignment with the forward end portion 30a of the output shaft 30. Rotation of the output shaft 30 of the motor 24 is thereby supplied through the coupler 26 to the flossing member 20.

In the illustrated embodiment of the flossing member 20, the side flossing filaments 42 and the central flossing filament 34 are integrally formed as a molded plastic unit. The side flossing filaments 42 are arranged along the length of the intermediate portion 40 of the central flossing filament 34 in spaced apart pairs (11 pairs being illustrated in the drawings). The two side flossing filaments 42 of each pair extend generally transverse to the axis of the center flossing filament 34 in opposite directions, as shown by opposing side flossing filaments 42a and 42b of the pair of side flossing filaments shown enlarged in FIG. 5B.

The side flossing filaments 42 and the tip and intermediate portions 38 and 40 of the central flossing filament 34 have a generally circular cross-section, although other cross-sectional shapes may be used. The side flossing filaments 42 are substantially smaller in cross-sectional diameter than the central flossing filament. The tip and intermediate portions 38 and 40 of the central flossing filament 34 have a diameter of between 0.012 inches to 0.030 inches (a maximum average transverse dimension), preferably 0.016 inches to 0.020 inches. In the illustrated embodiment, the tip portion 38 and an adjacent lengthwise portion of the intermediate portion 40 have a diameter of 0.016 inches. A lengthwise portion of the intermediate portion 40, located toward the base portion 36, has a diameter of 0.020 inches. A lengthwise portion of the intermediate portion 40 therebetween has a diameter of 0.018 inches. For a person with normal size inter-dental spaces, use of the central flossing filament with the diameter of 0.030 inches may be almost too large to fit through the spaces. However, there are situations, such as when a person has tooth implant bars, implanted teeth, large bone loss or simply very large gaps between adjacent teeth, where the central flossing filament 34 may have a diameter of as much as 0.050 inches. Even in these situations, use of the central flossing filament with side flossing filaments is helpful.

Figure 5B:
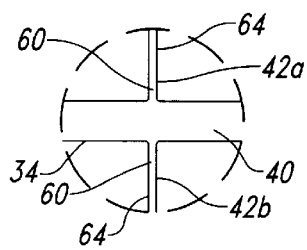
FIG. 5B is an enlarged top view of the flossing member of FIG. 5A showing the encircled portion indicated by broken line 5B where a pair of side filaments are attached to the central filament.
Figure 5C:
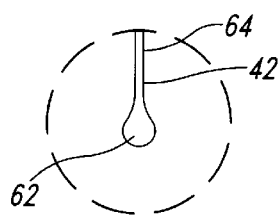
FIG. 5C is an enlarged top view of the flossing member of FIG. 5A showing the encircled portion indicated by broken line 5C where an enlarged end portion is attached to a free-end of one side filament.
Figure 5D:
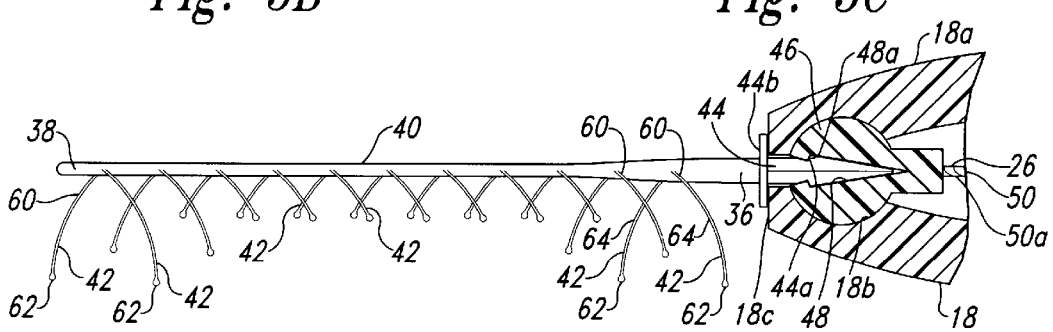
FIG. 5D is an enlarged, fragmentary view of the flossing device of FIG. 1 showing the flossing member attachment head and a supporting end portion of the flossing device in cross-section.

The side flossing filaments 42 each have an inward attachment end portion 60 fixedly attached to the intermediate portion 40 of the central flossing filament 34 (as best shown in FIG. 5B), a weighted free-end portion 62 (as best shown in FIG. 5C), and an elongated middle portion 64 extending between the weighted end portion and the attachment end portion. The side flossing filaments 42 are non-abrasive and their cleaning action results primarily from their impact or whacking against the tooth surfaces they contact as they whirl and whip about when spinning around the central flossing filament 34 as it rotates, as well as their stroking movement across the tooth surface. The elongated middle portion 64 has a diameter of between 0.002 inches to 0.008 inches (a maximum average transverse dimension), preferably 0.004 inches to 0.006 inches. The weighted end portion 64 has an enlarged tear or micro-ball shape which has a diameter of between 0.004 inches and 0.010 inches, preferably 0.010 inches. It is apparent that the side flossing filaments 42 have a more hair-like size and thread-like flexibility, and are thinner, less resilient and more flexible than the central flossing filament 34. The side flossing filaments 42, and especially the middle portions 64 thereof, are sufficiently thin and flexible so as to freely bend under the resistance encountered when the flossing member 20 is inserted between the adjacent teeth of a user for flossing, and have little resiliency.

The side flossing filaments 42 may have a uniform length, or as best shown in FIG. 5A, may vary in length according to their position along the length of the intermediate portion 40 of the central flossing filament 34. In the illustrated embodiment, the side flossing filaments 42 have a length of between 0.040 inches to 0.130 inches (average length) when measured between the outward ends of the weighted end portions 64 of an opposing pair of side flossing filaments (0.020 inches to 0.065 inches measured from the center of the central flossing filament intermediate portion to the outward end of the side flossing filament). Preferably, the longitudinally outermost opposing pair of side flossing filaments 42 toward the base and tip portions 36 and 38 of the central flossing filament 34 are the longest, having a combined weighted end to weighted end length of 0.130 inches. As such, if the diameter of the intermediate portion 40 of the central flossing filament 34 at which the opposing pair of side flossing filaments 42 are attached has a diameter of 0.016 inches (as in the illustrated embodiment toward the tip portion 38), the side flossing filaments each have a length of 0.057 inches.

The next longitudinal inward opposing pair of side flossing filaments 42 from each of the outermost pair preferably have a combined length of 0.090 inches. The remainder of the opposing pairs of side flossing filaments 42, located inward therefrom and along the central lengthwise portion of the intermediate portion 40, have a combined pair length of 0.040 inches. As will be described below, when the flossing member 20 is inserted between adjacent teeth of a user for their flossing, the shorter length side flossing filaments 42 along the central lengthwise portion of the intermediate portion 40 are positioned between the teeth, and the longer length side flossing filaments will be positioned toward the front and rear faces of the teeth, as shown in FIG. 7B.

The opposing pairs of side flossing filaments 42 are attached to the intermediate portion 40 of the central flossing filament 34 in spaced apart arrangement along the length of the intermediate portion. The opposing pairs of side flossing filaments 42 along the central lengthwise portion of the intermediate portion 40 are preferably spaced apart from the next adjacent opposing pair by 0.050 inches. The next longitudinally outward adjacent opposing pair of side flossing filaments 42 is preferably spaced outward therefrom by 0.030 inches. This opposing pair is preferably spaced inward from the longitudinally outermost adjacent opposing pair of side flossing filaments 42 by 0.045 inches. The illustrated embodiment of the flossing member 20 utilizes 16 opposing pairs of side flossing filaments 42, which requires the intermediate portion 40 of the central flossing filament 34 to have a length of at least 0.700 inches.

As will be more fully discussed below, the tip and intermediate portion 38 and 40 of the central flossing filament 34, with the side flossing filaments 42 attached, are configured to fit between the adjacent teeth and the interdental papilla of the user whose teeth are being flossed when endwise inserted therebetween. The flossing member 20 can be made of any material suitable for use in the human mouth which otherwise has suitable characteristics. At least the intermediate portion 40 of the central flossing filament 34 may be manufactured from a material such as plastic, metal wire, reinforced textile and the like having suitable flexibility and resiliency. The intermediate portion 40 of the illustrated embodiment has sufficient stiffness to be self-supporting but has sufficient flexibility and resiliency to effect a flossing action between the teeth of the user by imparting a flossing motion to the intermediate portion. It is desirable that the intermediate portion 40 have a memory and be impregnable to the environment of the mouth. For example, the intermediate portion 40 as well as the entire flossing member 20 may be manufactured of nylon. To provide the nylon central flossing filament 34 with sufficient stiffness and resiliency, the central flossing filament may be molded around a Nickel-Titanium alloy core wire (not shown) extending along the longitudinal axis of the central flossing filament. While the central flossing filament 40 must have sufficient stiffness to be inserted endwise between adjacent teeth and into the sulcus without substantial deformation of shape and without external support, the central flossing filament preferably has sufficient flexibility that if the tip portion 38 is inadvertently jabbed against the gums when attempting to insert the flossing member 20 between an inter-dental space it will harmlessly bend rather than stabbing and damaging the gums.

The tip and intermediate portion 38 and 40 are sized to be received between adjacent teeth of the user without the need to traverse any contract areas between the teeth from at least the front of the mouth of the user. The side flossing filaments 42 attached to the intermediate portion 40 of the central flossing filament 34 have sufficient flexibility to fold or bend back substantially against the intermediate portion when inserted between adjacent teeth, as best shown in FIG. 7A. As noted above, the side flossing filaments 42 are much smaller in cross-section than the intermediate portion 40 (for example, 0.004 inches verses 0.016 inches), and the combined thickness of the intermediate portion and the folded back side flossing filaments must be sufficiently small to allow them to be easily received between the adjacent teeth of the user at least when a drive force is not being supplied to the flossing member 20. The combined size is also sufficiently small that the intermediate portion 40 and folded back side flossing filaments 42 can be positioned in the sulcus between a tooth and the adjacent inter-dental papilla portion of the gum for effecting a flossing action therein.

The flossing device 10 provides a particularly convenient mechanism for effectively and efficiently accessing not only the tooth surfaces between the adjacent teeth for cleaning, but also the sulcus between the inter-dental papilla portions of the gum and the teeth, irrespective of contact areas between the teeth. Referring to FIGS. 2A and 2B, FIGS. 6A and 6B, and FIGS. 7A and 7B, the human mouth includes a plurality of adjacent teeth 70 disposed in the gums 72. Each tooth 70 typically includes a crown (body) portion 70a projecting above the associated gum 72, a root 70b connecting the tooth to bone below the gum, and a constricted neck portion 70c between the root and crown surrounded by the gum. In many instances, the relative dispositions of adjacent teeth 70 create contact areas 74 between the crowns 70a of the teeth, i.e., portions of the crowns of adjacent teeth touch or nearly touch. In many instances, such contact areas 74 make access to the pocket or inter-dental sulcus 76, the space between inter-dental papilla 72a and the neck portion 70c of the tooth 70, from above, as conventionally required for flossing with conventional flossing string, particularly difficult, if not impossible.

As noted above, the tip and intermediate portions 38 and 40 of flossing member 20, with the side flossing filaments 42 in folded back arrangement (see FIG. 7A), are dimensioned and configured to be received between the adjacent teeth 70. The intermediate portion 40 and, preferably the tip portion 38, are also dimensioned and configured to be received in the sulcus 76 between inter-dental papilla 72a and tooth 70 as best seen in FIGS. 6A and 6B. When driven for cleaning, the tip portion 38 is generally not positioned between the teeth 70 or on the sulcus 76, but is positioned inward of the teeth with only the intermediate portion 40 and at least some of the side flossing filaments 42 along the central lengthwise portion of the intermediate portion between the teeth or in the sulcus. Thus, the tip portion 38 does little, if any cleaning. The cleaning by the central flossing filament 34 is accomplished primarily by the sides of the intermediate portion 40 contacting the tooth surface. The side flossing filaments 42 provide increased flossing action. The tip portion 38 is not intended to clean in the sulcus 76 or between the adjacent teeth 70, but rather to pass therethrough with the intermediate portion 40 positioned therein for cleaning. The tip portion 38 as well as the intermediate portion 40 are in the illustrated embodiment too flexible to serve as a tooth pick.

While resilient in the illustrated embodiment, the central flossing filament 34 of the flossing member 20 is sufficiently stiff to maintain its shape, and thus is capable of being inserted into the inter-dental gap or space between teeth 70 and within the sulcus 76, irrespective of the contact area 74 that may exist by passing between teeth 70, preferably from the labial (front) direction but also possible from the lingual (back) direction, at a location between the contact areas 74 and the associated gum 72. The central flossing filament 34 also has sufficient tortional strength and stiffness to transmit the rotational force applied thereto by the motor 24 to the side flossing filaments 42 to supply them with adequate rotational drive force. A flossing action is realized through motion of flossing member 20 when situated between the adjacent teeth 70, or in the sulcus 76, as shown in FIGS. 2A, 2B, 6B, and 7B, and as will be described in greater detail below.

In operation, the actuation of the electric switch 28 completes an electrical circuit to energize the electric motor 24 with the power supply 22 to rotate the output shaft 30 of the motor, either in a unidirectional rotational movement or in a quickly reciprocating rotational movement (i.e., alternating between clockwise and counterclockwise rotation which tends to increase the whipping motion of the side flossing filaments). If desired, the switch 28 can have multiple settings for different speeds of the motor 24. While operating, the rotational drive output of the output shaft 30 of the electric motor 24 rotates the coupler 26. As previously stated, the shaft connector 52 of the coupler 26 is attached to the forward end portion 30a of the output shaft 30 and transmits the rotational output of the output shaft to the flossing member 20 attached by the connector member 44 of the base portion 36. The motor 24 has a rotational speed high enough to cause the rotational speed of the central flossing filament 34 to be sufficient that a centrifugal force on the flexible side flossing filaments 42 results which causes them to extend outward in response thereto, extending more radially outward and away from the central flossing filament than when in a stationary, limp condition. When not in contact with the teeth the speed is sufficient to extend the side flossing filaments substantially radially outward. As a consequence, the side flossing filaments 40 are caused to whip and flail about with sufficient speed that when contacting the tooth surface, the engaged plaque on the tooth surface is dislodged and moved away. In the illustrated embodiment, a rotational speed of the motor 24 between 600 and 20,000 revolutions per minute (RPMs) is used. This produces a similar speed and direction rotation for the central flossing filament 34 and the side flossing filaments 42.

Due to the rapid rotation of the central flossing filament 34 that results, initially about the stationary longitudinal axis 32 and then about the driven longitudinal axis of the flossing member 20, the tip portion 38 and the elongated intermediate portion 40 of the elongated central flossing filament 34 are imparted with a flossing action and whip or flail about to effect the desired flossing action between two teeth 70 or between one of the teeth 70 and associated gum 72, such as between the neck portion 70c of the tooth and the inter-dental papilla 72a when the intermediate portion is in the sulcus 76, such as shown in FIGS. 6B and 7B. Thus, the tooth can be cleaned below the inter-dental papilla. When driven, the intermediate portion 40 is driven to move along a generally conical path of travel to produce its flossing motion and the side flossing filaments 42 move therewith and spin about the intermediate portion as it moves along. As noted above, the flossing action of the intermediate portion 40 results from the whipping or flailing intermediate portion 40 impacting against the inter-proximal tooth surface and stroking the contacted tooth surface.

The side flossing filaments 42 attached to the central flossing filament 34 provide increased effectiveness and efficiency for the flossing member 20 when flossing. The rapid rotation of the central flossing filament 34 applies a radially outward directed centrifugal force on the flexible side flossing filaments 42 to cause them to move outward from their stationary drooping position as shown in FIG. 5D or their initially folded back position adjacent to the intermediate portion 40 of the central flossing filament which resulted upon insertion of the central flossing filament between the adjacent teeth 70 as shown in FIG. 7A. The position of the side flossing filaments 42 when driven with a rotational drive is shown in FIGS. 2A, 2B, 6B, and 7B. The side flossing filaments 42 whirl and whip about the central flossing filament 34 when so driven much as a stone which is whirled about on the end of a string. This centrifugally whipping motion of the side flossing filaments 42 is enhanced by the use of the weighted free-end portion 62 of each side flossing filament which increases the centrifugal force applied to the side flossing filament by the rotation of the central flossing filament 34 and hence increases the impact with the tooth surface over that which would be experienced without use of a weighted free-end portion. It is noted, however, that the side flossing filaments will still promote increased effectiveness and efficiency of flossing even if weighted free-end portions are not used.

With the flossing device 10 using the flossing member 20 of the present invention, not only does the whipping motion of the central flossing filament 34 hitting against the tooth surface as it whips about produce a flossing action which cleans the teeth contacted, the contact of the spinning side flossing filaments 42 against the tooth surface also clean the tooth contacted. It is noted that a cleaning action by the spinning side flossing filaments 42 results from contact by any portion of the side flossing filament, whether it be the attachment end portion 60, the elongated middle portion 64 or the weighted free-end portion 62, although the most significant improved cleaning action is believed to result from contact by the elongated middle portions and weighted free-end portions of the side flossing filaments. The flossing action produced by the side flossing filaments 42 cleans by their impact or whacking against the tooth surface to loosen bacteria plaque, but also by their stroking or wiping movement across the tooth surface that results, to further dislodge and wipe away plaque. This flossing action is achieved without sufficient abrasion or impact to damage the teeth being cleaned.

The spinning side flossing filaments 42 not only engage and clean the inter-proximal surfaces of the teeth 70, and also the neck portion 70c of the teeth at the sulcus 76. The side flossing filaments 42 have sufficient length to also clean substantial portions of the front and back surfaces of the teeth, especially the longer side flossing filaments located toward the base and tip portions 36 and 38 of the central flossing filament 34. These surfaces receive little, if any, cleaning contact with the intermediate portion 40 of the central flossing filament 34, which primarily cleans only the interproximal tooth surfaces. Even the cleaning of the inter-proximal tooth surfaces is improved by the shorter length side flossing filaments 42 which are attached along the central lengthwise portion of the intermediate portion 40 of the central flossing filament 34.

The flossing device 10 may be used by inserting the flossing member 20 from the front and into the inter-dental space between the adjacent teeth 70, between the gum 72 and the contact area 74, sufficiently far to position the tip portion 38 inward beyond the teeth and to position the shorter length side flossing filaments 42 between the teeth for contacting the inter-proximal tooth surfaces. As such, the longer length side flossing filaments toward the base and tip portions 36 and 38 of the central flossing filament 34 may be positioned at the front and rear surfaces, respectively, of the teeth to contact and simultaneously clean these surfaces. Not only are the inter-proximal tooth surfaces better cleaned using the side flossing filament 42 of the present invention, but so are the front and rear surfaces of the teeth 70 between which the flossing member 20 is inserted.

Once the flossing member 20 is in the desired position between the teeth 70 or in the sulcus 76, the switch 28 is actuated to activate the flossing motion of the central flossing filament 34 and the flossing motion of the side flossing filament 42. The user, grasping and moving up and down and about the case 12 of the flossing device 10, can similarly move the flossing member 20 up and down and about between the teeth 70 and into and out of the sulcus 76, with the resulting motion of the intermediate portion 40 of the flossing member 20 and the side flossing filaments 42 described above, efficiently and effectively flossing the teeth 70. This requires little effort, skill or time by the user. While up and down and about movement of the flossing member 20 is described, the whipping action of the central flossing filament 34 and the spinning side flossing filaments 42 may require very little motion by the user, if any, depending on the length of the side flossing filaments and the size of the interdental space between the teeth 70 being flossed.

It is noted that while the side flossing filaments 42 when driven with a rotational drive force spin about the driven longitudinal axis of the central flossing filament 34, their contact with the teeth 70 causes them to depart from a purely circular circumferential path of travel and creates more of a flailing action against the tooth surface. It is also noted that while the side flossing filaments 42 are shown attached to the intermediate portion 40 of the central flossing filament 34 at right angles thereto, attachment at other angles is possible. In one embodiment not illustrated, the longer side flossing filaments 42 toward the tip portion 38 are slanted rearward so as to tilt toward the rear surface of the teeth and the side flossing filaments toward the base portion 36 are slanted forward so as to tilt toward the front surface of the teeth when initially positioned for use within the inter-dental space as described above. However, the high degree of flexibility of the side flossing filaments used to promote the spinning action under the centrifugal force applied, makes such angled attachment not particularly beneficial in controlling the tooth surface engaged thereby or the degree of flossing action generated.

When the flossing is complete, the user actuates the switch 28 to deactivate the flossing motion of the flossing member 20 and it is withdrawn from between the teeth 70 just flossed and inserted between the next pair of teeth to be flossed or returned to a storage unit (not shown) having a built-in battery charger for the battery 22. The flossing member 20 should be rinsed after being used. At any time desired, with the flossing member 20 withdrawn from the mouth and deactivated, the flossing member may be removed and replaced with a new flossing member or the personal flossing filament belonging to the family member intending to next use the flossing device 10. It is contemplated that the flossing member 20 will have an inexpensive construction and be disposed of when worn, broken, or dirty.

The removal of the flossing member 20 is achieved by simply pulling outward thereon, away from the coupler support 18, preferably while grasping the forward end portion 18*a* of the coupler support, to dislodge the connector member 44 of the central flossing filament 34 from the socket 48 of the attachment head 46 of the coupler 26. The coupler support 18 need not be removed from attachment head 46 or from the boot 14. To attach the same or a different flossing member 20 to the flossing device 10, the connector member 44 is aligned with the socket 48 and pushed into the socket until it snaps into place within the socket, with the shoulder portions 48*a* of the socket 48 engaging the corresponding shoulder portions 44*a* of the connector member, as shown in FIG. 5D. The connector member 44 includes a circumferential flange 44*b* in sealing engagement with an end surface 18*c* at the forward end portion 18*a* of the coupler support 18 about the open end of the socket 48 to provide at least a partial fluid seal and keep foreign material out of the socket during use of the flossing device 10.

If it is desired to remove the boot 14 or the coupler support 18 for cleaning, or to remove the coupler 26 for repair, replacement or cleaning, the boot, coupler support and coupler may be easily and quickly removed and reassembled. First, it is preferably to remove the flossing member 20 from the attachment head 46 of the coupler 26. As stated above, the coupler support 18 is removably snap fit within the forward end 14*a* of the boot 14, and the boot is removably snap fit over the forward end 12*a* of the case 12, and they may be disconnect by pulling them apart. Both the coupler support 18 and the boot 14 are preferably manufactured from a resilient material. As also stated above, the shaft connector 52 of the coupler 26 removably receives the forward end portion 30*a* of the output shaft 30 therein, and the spherical socket 18*b* of the coupler support 18 removably receives the spherical attachment head 46 therein, and they may be disconnected by pulling them apart. The attachment head 46 is best removed from the socket 18*b* by moving the attachment head through the rearward opening in the coupler support 18. As noted above, the coupler support 18 is manufactured from a resilient material. To reassemble the components they are simply aligned and pushed back together. Of course, the disassembly and assembly should occur when the motor 24 is not energized.

While not illustrated, the flossing device 10 may be constructed with a fluid reservoir and pump to supply fluids, such as medicaments to the gums and teeth, such as described in U.S. Pat. No. 5,573,020, using a central flossing filament having a coaxial conduit therein, or in any other suitable manner.

A first alternative embodiment of the flossing device 10 is shown in FIG. 8. For ease of understanding, the same or similar components of alternative embodiments will be similarly numbered with those of the embodiment of FIG. 1. Further, only differences in construction or operation will be described in detail.

Referring again to FIG. 8, the flossing device 10 is similar in most regards except that the case 12 has an elongated, reduced diameter neck portion which terminates at the forward end 12*a* with a reduced diameter opening. Further, the output shaft 30 of the motor 24 extends almost fully to the forward end 12*a* of the case 12. In this embodiment, the boot 14 is not used and the coupler support 18 is removably snap fit within the forward end 12*a* of the case 12. As before, the coupler 26 has the shaft connector 52 coupled to the forward end portion 30*a* of the output shaft 30. In FIG. 8, the flossing member is shown disconnected from the attachment head 46 of the coupler 26. The coupler 26 and coupler support 18 arrangement is particularly useful to retrofit an existing model of an electric tooth flosser and any similarly constructed product using a rotational drive for use with the flossing member 20 of the present invention having side flossing filaments 42. In such a manner, existing products can be converted to use the flossing member 20, with the coupler and coupler support serving as an adapter.

A second alternative embodiment of the flossing device 10 is shown in FIG. 9A. In this embodiment, the shaft connector 52 attached to the forward end portion 30*a* of the output shaft 30 has an eccentric arm portion 52*a* extending transverse to the output shaft with the rearward end portion 50*b* of the drive cable 50 fixedly attached to the eccentric arm portion 52*a* at a position out of axial alignment with the drive shaft to provide an eccentric drive to the coupler 26. Thus, the driving force to the drive cable 50 and the flossing member 20 is supplied from the output shaft 30 out of alignment with the central flossing filament 34. As a result, the rearward portion 50*b* of the drive cable 50 experiences rotational movement about its longitudinal axis and also a translatory movement (X-Y movement) in a plane transverse to the output shaft 30, with the translatory movement being off and about the axis of the output shaft (tracing out a circular path thereabout). The path traveled is determined by the length of the eccentric arm portion 52*a*. It is noted that the rearward opening in a rearward end 18*d* of the coupler support 18 has a smaller diameter than the length of the eccentric arm portion 52*a*, measured between the longitudinal axis of the output shaft 30 and the attachment of the drive cable rearward end portion 52*b* to the eccentric arm portion.

As previously described, the generally spherical attachment head 46 is received in a generally spherical socket 18*b* of the coupler support 18, so that the attachment head is rotatable therein about the axis of the forward end portion 50*a* of the drive cable 50 as the drive cable 46 rotates in response to a rotational drive force component. The attachment head 46 may also rock back and forth therein in response to a translatory drive force component transmitted thereto by the drive cable 50 as a result of the rearward end portion 50*b* thereof being moved about off the axis of the output shaft 30. The rotational and translational drive components experienced by the attachment head 46 are transmitted to the connector member 44 of the central flossing filament 34 of the flossing member 20. The result of the displaced attachment of the drive cable 50 relative to the longitudinal axis of the output shaft 30, and the interaction of the attachment head 46 with the coupler support 18, effects movement of the flossing member with both rotational and translatory drive components and results in both rotational and translatory movement of flossing member 20. The movement for a pair of side flossing filaments 42 as the central flossing filament 34 responds to a single, full revolution of the output shaft 30, at full operational speed and without interference from contact with teeth, is shown schematically in FIG. 9B. The opposing pair of side flossing filaments are labeled "a" and "b" and shown in solid line at the position which will be used as the initial position for purposes of discussion.

As can be seen in FIG. 9B, at the initial position shown in solid line, the side flossing filaments 42 labeled "a" and "b" are fully extended under the centrifugal force applied thereto by rotation of the central flossing filament 34 about its driven longitudinal axis. They are shown as rotating counterclockwise when viewed from the tip portion 38 as a result of the counterclockwise rotation of the output shaft 30 and the drive cable 50. This counterclockwise rotation tends to cause the tip portion 33 of the central flossing filament 34 to whip about a generally circular path with the center being at about the location where the base portion 36 is attached to the attachment head 46. As the central flossing filament 34 so moves counterclockwise relative to the attachment head 46, among the eight selected positions shown in FIG. 9B having a 45° separation therebetween, the side flossing filaments 42 move therewith, but also experience counter-clockwise rotation about the driven longitudinal axis of the central flossing filament. For each position of the central flossing filament 34 shown in FIG. 9B the side flossing filaments 42 rotate relative to the driven longitudinal axis of the central flossing filament by 45°. This whipping about of both the central flossing filament 34 and the side flossing filament 42 creates the flossing action used to clean the teeth 70.

A third alternative embodiment of the flossing device 10 is shown in FIG. 10–13. In this embodiment, only a translation or oscillatory drive force component is supplied to the flossing member 20. The motor 24 has an eccentric drive member 31 which serves as a cam attached to the end of the output shaft 30. The rotational drive force supplied by the motor 24 is converted or translated into an oscillating drive producing a linear translation or translatory movement of the flossing member 20 by an articulated drive arm assembly 80 which serves as a coupler coupling the drive force of the motor 24 to the flossing member 20. The drive arm assembly 80 includes a rigid rearward arm 82 and a rigid forward arm 84, shown in greater detail in FIGS. 12 and 13 removed from the case 12. The rearward arm 82 has at a rearward end thereof a pair of rearward projecting, spaced apart cam follower members 86 defining an opening therebetween sized to receive the eccentric drive member 31. The cam follower members 86 translate rotational movement of the eccentric drive member 31 caused by rotation of the output shaft 30 of the motor 24 into rocking or oscillating movement of the rearward arm 82 about a pivot pin 88 formed integral with the rearward arm and supported at a fixed location by the case 12. The pivot axis of the pivot pin 88 is transverse to the longitudinal axis of the output shaft 30. The rearward arm 82 is free to oscillate about the pivot axis of the pivot pin 88, as such, when the eccentric drive member 31 drives the cam follower members 86 in a direction transverse to the pivot axis of the pivot pin 88 (such as the upward direction shown in FIG. 10), the rearward arm rotates about the pivot axis of the pivot pin 88 in a counterclockwise direction and a forward end of the rearward arm moves in the opposite linear direction (such as the downward direction shown in FIG. 10), producing an arcuate movement at the forward end of the rearward arm. The opposite reciprocating movement results when the cam follower members 86 are moved in the opposite direction (see FIG. 11) by the eccentric drive member 31.

A forward end of the rearward arm 82 includes a pair of laterally spaced apart pivot forks 90, each having a forwardly opening slot 92 therein. The pivot forks 90 and the slots 92 therein are arranged to each slidably and rotatably receive opposite end portions of pin 94, formed integral with the forward arm 84 at its rearward end, in parallel alignment with the pivot axis of the pivot pin 88. The forward end of the forward arm 84 has formed integral therewith an attachment head 96 which serves the same general purpose of the attachment head 46 of the coupler 26, except that rather than the socket 48, the attachment head 96 includes a pair of jaws 96a and 96b which removably receive the connector member 44 of the central flossing filament 34 therein. The attachment head 96 has a partial cylindrical outer shape and is rotatably received in a correspondingly shaped and sized cylindrical socket 98 formed in the forward end 12a of the case 12 for rotation of the forward end of the forward arm 84 about an axis of rotation in parallel alignment with the pivot axis of the pivot pin 88. In this third alternative embodiment the case 12 may be fabricated from a somewhat resilient material and the boot 14 and coupler support 18 of the embodiment of FIG. 1 are integrated into the case design.

As previously described, the rotational drive output of the motor 24 is translated into arcuate movement of the forward end of the rearward arm 82. This movement is transmitted to the rearward end of the forward arm 84 through the pivot forks 90 engaging the pin 94 to move the rearward end of the forward arm in arcuate movements (in the up and down directions shown in FIGS. 10 and 11). The rearward and forward arms 82 and 84 move through a plane parallel to the output shaft axis. Since the attachment head 96 is restrained to have substantially only rotational movement within the socket 98 in the forward end 12a of the case 12, the arcuate movement of the rearward end of the forward arm 84 about the rotational axis of the attachment head produces a rocking or oscillatory movement of the attachment head 96 about an axis transverse to the axis of the output shaft 30 of the motor 24. The slots 92 in the pivot forks 90 allow the slight forward and rearward movement of the pin 94 that result because the attachment head 96 is so restrained.

The oscillation of the attachment head 96 about its rotational axis is transmitted to the central flossing filament 34 of the flossing member 20 which is held by and extends from the attachment head 96 generally transverse to the attachment head rotational axis. The result is the supply of a drive force to the flossing member 20 with only a translatory component. The flossing member 20 is moved with a component of motion out of alignment with the stationary longitudinal axis to produce the flossing motion. The flossing member 20 is reciprocally moved along a generally translatory path of travel in response to the oscillatory drive. The rotational speed of the motor 24 and the arrangement of the articulate drive arm assembly 80 produces a rapid oscillatory movement of the flossing member 20. The resulting flossing motion of the flossing member 20 is illustrated schematically in FIGS. 14A and 14B for the central flossing filament 34 and only one opposing pair of side flossing filaments 42.

Figure 14A:
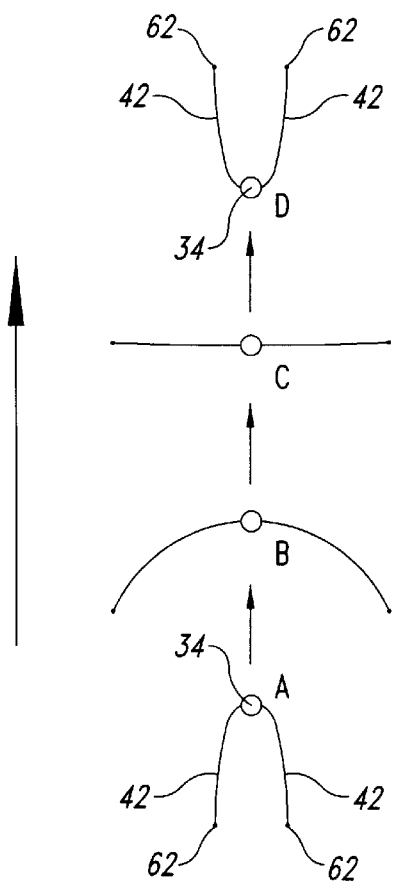
FIG. 14A is a schematic end view of the flossing member used with the third alternative embodiment of FIG. 10 shown in various positions when the translation arm provides an upward translational drive force thereto.
Figure 14B:
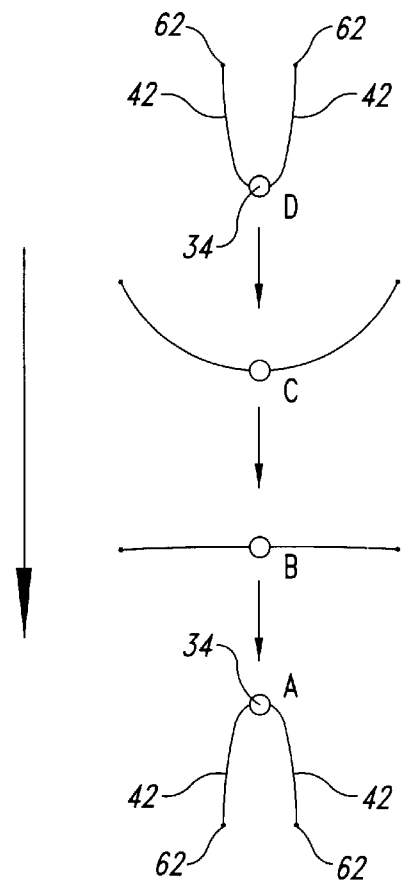
FIG. 14B is a schematic end view of the flossing member used with the third alternative embodiment of FIG. 10 shown in various positions when the translation arm provides a downward translational drive force thereto.

The central flossing filament 34 is shown in FIG. 14A moving upward between 4 sequential positions indicated by letters A through D, and in FIG. 14B moving downward between four sequential positions indicated in reverse order by the same letters. Positions C and B in both FIGS. 14A and 14B are the positions that corresponds to the end limits of translatory travel of the flossing member 20 that would result from the full range of oscillation of the attachment head 98 (shown in FIGS. 10 and 11) were it not for the central flossing filament 34 being manufactured from a flexible and resilient material. For upward travel, the central flossing filament 34 starts at position A. It is noted that the central flossing filament 34 starts its upward movement at position A only because it has flexed downward under the downward momentum of the flossing member 20 beyond position B whereat the attachment head 98 changes rotational direction from the prior downward movement. As the central flossing filament 34 moves downward during the prior downward movement from position B to position A it is decelerating, causing the momentum of the side flossing filaments 42 to carry them further downward and toward each other more than when just reaching position B (see FIG. 14B). As such, sometime after the upward rotation of the attachment head 96 starts, the central flossing filament 34 and the side flossing filaments 42 will finally exhaust their downward momentum at position A of FIG. 14A and begin their upward travel to position B, resulting in the side flossing filaments spreading apart again.

When the upward moving central flossing member 34 reaches position C, the attachment head 98 again reverses its rotational direction to the downward direction. The momentum of the central flossing filament 34 and the side flossing filaments 42, and the flexible and resilient nature of both cause them to continue raveling upward until reaching position D whereat the central flossing filament and the side flossing filaments have exhausted their upward momentum. Because of the greater flexibility of the side flossing filaments 42 compared with the central flossing filament 34, the momentum of the side flossing filaments cause them to move further upward than the central flossing filament and to move toward each other.

As shown in FIG. 14B, at position D the downward movement of the flossing member 20 commences. The downward movement continues until reaching position A of FIG. 14B whereat upward movement begins again. In this and all other of the embodiments, the resulting motion of both the central flossing filament 34 and the side flossing filaments 42 produces a whipping or flailing movement of the side flossing filaments to provide a more effective and efficient flossing action than achieved by the use of a central flossing filament without side flossing filaments. In the embodiment of FIGS. 10–13, no rotational drive force component is supplied to the side flossing filaments 42 and thus they do not spin about the central flossing filament 34.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. An apparatus for cleaning the surfaces of teeth in a human mouth, comprising:
   a flexible, resilient central flossing filament including a base portion, a free-end portion, and an elongated intermediate portion located between said central filament base portion and said central filament free-end portion;
   a plurality of flexible side flossing filaments, each having an attachment end portion fixedly attached to said central filament intermediate portion, a free-end portion and an elongated intermediate portion located between said side filament attachment portion and said side filament free-end portion;
   said central filament intermediate and free-end portions, with said side flossing filaments attached thereto, being sized to be received between adjacent teeth without traversing any contact areas between the adjacent teeth from at least the front of the mouth, said central filament intermediate portion being composed of a material having sufficient flexibility and resiliency to effect a first flossing action between the adjacent teeth without damage to the teeth by imparting a first flossing motion to said central filament intermediate portion, said central filament intermediate portion extending along a longitudinal extension line when not moving, said central flossing filament having sufficient stiffness to be self-supporting and support said side flossing filament without significant bending;
   said side flossing filaments being attached at spaced apart locations along said central filament intermediate portion to be at positions between the adjacent teeth and adjacent to at least one of a forward surface and a rearward surface of the adjacent teeth when said central filament intermediate portion is received between the adjacent teeth;
   said side filament intermediate portions being composed of a material having sufficient flexibility to effect a second flossing action between the adjacent teeth and at one of said forward surface and said rearward surface of the adjacent teeth by imparting a second flossing motion to said side flossing filaments;
   a motive source; and
   a coupling connecting said central filament base portion to said motive source and moving said central filament intermediate portion among a plurality of positions substantially out of alignment with said longitudinal line to impart said first flossing motion to said central filament intermediate portion and said second flossing motion to said side flossing filaments.

2. The apparatus of claim 1 wherein at least said central filament intermediate portion, with said side flossing filaments attached thereto, are sized to be received in the sulcus between a tooth of the adjacent teeth and the adjacent inter-dental papilla portion of the gum for effecting said first and second flossing actions therein.

3. The apparatus of claim 1 wherein said motive source produces a rotational output drive and said coupling supplies said rotational output drive to said central filament base portion to produce said first flossing motion of said central filament intermediate portion and said second flossing motion of said side flossing filaments.

4. The apparatus of claim 3 wherein said motive source is rotatably connected by said coupling to said central flossing filament base portion and rotates said central flossing filament about a driven longitudinal axis thereof with sufficient speed to whirl said side flossing filaments about said central flossing filament and whip said side flossing filaments against the adjacent teeth.

5. The apparatus of claim 4 wherein said rotation of said central flossing filament is transmitted to said side flossing filaments to rotate said side flossing filaments about said central filament driven longitudinal axis as said central flossing filament rotates thereabout.

6. The apparatus of claim 1 wherein said motive source produces a rotational output drive and said coupling translates said rotational output drive into at least one of a rotational drive and a translational drive which is supplied to said central filament base portion to move said central filament intermediate portion among said plurality of positions and thereby produce said first flossing motion of said central filament intermediate portion and said second flossing motion of said side flossing filaments, said drive supplied to said central base portion being at a sufficient speed to whip said side flossing filaments against the adjacent teeth.

7. An apparat us for cleaning the surfaces of teeth in a human mouth, comprising:
- a flexible, resilient central flossing filament including a base portion, a free-end portion, and an elongated intermediate portion located between said central filament base portion and said central filament free-end portion;
- at least one flexible side flossing filament having an attachment end portion attached to said central filament intermediate portion, a free-end portion and an elongated intermediate portion located between said side filament attachment portion and said side filament free-end portion;
- said central filament intermediate and free-end portions, with said side flossing filament attached thereto, being sized to be received between adjacent teeth without traversing any contact areas between the adjacent teeth from at least the front of the mouth, said central filament intermediate portion being sufficiently flexible and resilient to effect a first flossing action between the adjacent teeth by imparting a first flossing motion to said central filament intermediate portion;
- said side flossing filament being attached at a location along said central filament intermediate portion to be at one of a position between and a position adjacent to the adjacent teeth when said central filament intermediate portion is received therebetween;
- said side filament intermediate portion being sufficiently flexible to effect a second flossing action by imparting a second flossing motion to said side flossing filament;
- a motive source; and
- a coupling connecting said central filament base portion to said motive source, said coupling applying a moving force to said central filament intermediate portion with at least one of a rotational and a translational component to impart said first flossing motion to said central filament intermediate portion and said second flossing motion to said side flossing filament, said moving force being applied by said coupling with at least one of speed and rate of change of direction sufficient to whip said side flossing filament against the adjacent teeth.

8. The apparatus of claim 7 wherein at least said central filament intermediate portion, with said side flossing filament attached thereto, are sized to be received in the sulcus between a tooth of the adjacent teeth and the adjacent inter-dental papilla portion of the gum for effecting said first and second flossing actions therein.

9. The apparatus of claim 7 having a plurality of said side flossing filaments and wherein at least one of said side flossing filaments has a sufficient length and is attached to said central filament intermediate portion at a location to be positioned to engage a forward surface of the adjacent teeth, and wherein at least one of said side flossing filaments has a sufficient length and is attached to said central filament intermediate portion at a location to be positioned to engage a rearward surface of the adjacent teeth when said central filament intermediate portion is received between the adjacent teeth.

10. An apparatus for cleaning the surfaces of teeth in a human mouth, comprising:
- a flexible, resilient central flossing filament including a base portion, a free-end portion, and an elongated intermediate portion located between said central filament base portion and said central filament free-end portion;
- a plurality of flexible side flossing filaments, each having an attachment end portion attached to said central filament intermediate portion, a free-end portion and an elongated intermediate portion located between said side filament attachment portion and said side filament free-end portion;
- said central filament intermediate and free-end portions, with said side flossing filaments attached thereto, being sized to be received between adjacent teeth without traversing any contact areas between the adjacent teeth from at least the front of the mouth, said central filament intermediate portion being sufficiently flexible and resilient to effect a first flossing action between the adjacent teeth by imparting a first flossing motion to said central filament intermediate portion;
- said side flossing filaments being attached at spaced apart locations along said central filament intermediate portion to be at one of a position between and a position adjacent to the adjacent teeth when said central filament intermediate portion is received therebetween;
- said side filament intermediate portions being sufficiently flexible to effect a second flossing action by imparting a second flossing motion to said side flossing filament;
- a motive source; and
- a coupling connecting said motive source to said central flossing filament to impart said first flossing motion to said central filament intermediate portion and said second flossing motion to said side flossing filaments.

11. The apparatus of claim 10 wherein at least said central filament intermediate portion, with said side flossing filaments attached thereto, are sized to be received in the sulcus between a tooth of the adjacent teeth and the adjacent inter-dental papilla portion of the gum for effecting said first and second flossing actions therein.

12. The apparatus of claim 10 wherein said side flossing filaments are sufficiently flexible to bend back against said central filament intermediate portion upon insertion between the adjacent teeth, and at least said central filament intermediate portion, with said side flossing filaments attached thereto and bent back thereagainst, are sized to be received in the sulcus between a tooth of the adjacent teeth and the adjacent inter-dental papilla portion of the gum for effecting said first and second flossing actions therein.

13. The apparatus of claim 10 wherein said central filament intermediate portion extends along a longitudinal extension line when not moving, and said coupling moves said central flossing filament with a component of motion out of alignment with said longitudinal line to impart said first flossing motion to said central filament intermediate portion and said second flossing motion to said side flossing filaments in response to operation of said motive source, said component of motion having at least one of speed and rate of change of direction sufficient to whip said side flossing filaments against the adjacent teeth.

14. The apparatus of claim 10 wherein said coupling applies a moving force to said central flossing filament with at least one of a rotational and a translational component to impart said first flossing motion to said central filament intermediate portion and said second flossing motion to said side flossing filaments.

15. The apparatus of claim 10 wherein said coupling applies a moving force to said central flossing filament with a rotational component to move said central filament intermediate portion along a generally conical path of travel to produce said first flossing motion of said central filament intermediate portion and said second flossing motion of said side flossing filaments.

16. The apparatus of claim 10 wherein said motive source has a rotational output drive shaft and said coupling includes a drive cable with a shaft engagement end portion attachable to said output shaft and a flossing member attachment end portion to which said central filament base portion is releasably attached, and a coupler support rotatably supporting said flossing member attachment portion to permit rotation thereof in response to rotation of said drive cable by said motive source.

17. The apparatus of claim 10 wherein said motive source produces a rotational output drive and said coupling supplies said rotational output drive to said central flossing filament to produce said first flossing motion of said central filament intermediate portion and said second flossing motion of said side flossing filaments.

18. The apparatus of claim 10 wherein said motive source produces an output drive and said coupling translates said output drive into at least one of a rotational drive and a oscillatory drive which is supplied to said central flossing filament to produce said first flossing motion of said central filament intermediate portion and said second flossing motion of said side flossing filaments.

19. The apparatus of claim 18 wherein said output drive is a rotational output drive.

20. The apparatus of claim 19 wherein said coupling translates said output drive into said rotational drive of said central flossing filament at a sufficient rotational speed to produce centrifugal force on said side flossing filaments attached thereto sufficient to extend said side flossing filaments substantially radially outward.

21. The apparatus of claim 18 wherein said output drive is a rotational drive, and said coupling translates said output drive into said oscillatory drive of said central flossing filament at a sufficient translatory speed to cause said side flossing filaments attached thereto to whip about.

22. The apparatus of claim 10 wherein said motive source is a motor producing a rotational output and said coupling converts said rotational output into a moving force applied to said central flossing filament which moves said central flossing filament along a path of travel substantially out of alignment with said central flossing filament when at rest to effect said first flossing motion of said central filament intermediate portion and said second flossing motion of said side flossing filaments.

23. The apparatus of claim 22 wherein said moving force applied to said central flossing filament rotates said central flossing filament as said central flossing filament is moved along said path of travel.

24. The apparatus of claim 10 wherein said motive source supplies a moving force and said coupling applies said moving force to said central flossing filament with a force component out of longitudinal alignment with said central flossing filament to effect said first flossing motion of said central filament intermediate portion and said second flossing motion of said side flossing filaments.

25. The apparatus of claim 24 wherein said central filament intermediate portion has sufficient flexibility to bend outward under said moving force applied to said central flossing filament, and said coupling supplies said moving force with said force component sufficient to bend outward said central filament intermediate portion and move said bent central filament intermediate portion about to effect said first flossing motion of said central filament intermediate portion.

26. The apparatus of claim 10 wherein said central flossing filament has sufficient flexibility to bend under a moving force applied thereto by said coupling to produce said first flossing motion.

27. The apparatus of claim 10 wherein said motive source is rotatably connected by said coupling to said central flossing filament and rotates said central flossing filament about a driven longitudinal axis thereof.

28. The apparatus of claim 27 wherein said motive source rotates said central flossing filament with sufficient speed to produce centrifugal force on said side flossing filament sufficient to move said side filament intermediate portions outward.

29. The apparatus of claim 27 wherein said central flossing filament is sufficiently flexible to bend outward under the centrifugal force thereon resulting from rotation of said central flossing filament by said motive source.

30. The apparatus of claim 29 wherein said rotation of said central flossing filament is transmitted to said side flossing filaments to rotate said side flossing filaments about said central filament driven longitudinal axis as said central flossing filament rotates thereabout.

31. The apparatus of claim 27 wherein said rotation of said central flossing filament is transmitted to said side flossing filaments to rotate said side flossing filaments about said central filament driven longitudinal axis as said central flossing filament rotates thereabout.

32. The apparatus of claim 10 wherein said motive source is an electric motor producing a rotational output and said coupling converts said rotational output into a moving force applied to said central flossing filament.

33. The apparatus of claim 32 wherein said electric motor has a rotational output drive shaft and said coupling includes a drive cable with a shaft engagement end portion attachable to said output shaft and a flossing member attachment end portion to which said central filament base portion is releasably attached, and a coupler support rotatably supporting said flossing member attachment portion to permit rotation thereof in response to rotation of said drive cable by said electric motor.

34. The apparatus of claim 10 wherein at least one of said side flossing filaments has a sufficient length and is attached to said central filament intermediate portion at a location to be positioned to engage a forward surface of the adjacent teeth, and wherein at least one of said side flossing filaments has a sufficient length and is attached to said central filament intermediate portion at a location to be positioned to engage a rearward surface of the adjacent teeth when said central filament intermediate portion is received between the adjacent teeth.

35. An apparatus for cleaning the surfaces of teeth in a human mouth, comprising:

an elongated central member including a base portion, a free-end portion, and an elongated intermediate portion located between said central member base portion and said central member free-end portion;

at least one flexible side flossing filament having an attachment end portion attached to said central member intermediate portion, a free-end portion and an elongated intermediate portion located between said side filament attachment portion and said side filament free-end portion;

said central member intermediate and free-end portions, with said side flossing filament attached thereto, being sized to be received between adjacent teeth without traversing any contact areas between the adjacent teeth from at least the front of the mouth;

said side flossing filament being attached at a location along said central member intermediate portion to be at a position to contact at least one of the adjacent teeth when said central member intermediate portion is received between the adjacent teeth;

said side filament intermediate portion being sufficiently flexible to effect a flossing action against the one of the adjacent teeth contacted by imparting a flossing motion to said side flossing filament;

a motive source; and a coupling connecting said motive source to said central member filament to impart said flossing motion to said side flossing filament.

36. An apparatus for cleaning the surfaces of teeth in a human mouth, comprising:

an elongated central member including a base portion, a free-end portion, and an elongated intermediate portion located between said central member base portion and said central member free-end portion;

a plurality of flexible side flossing filaments, each having an attachment end portion attached to said central member intermediate portion, a free-end portion and an elongated intermediate portion located between said side filament attachment portion and said side filament free-end portion;

said central member intermediate and free-end portions, with said side flossing filaments attached thereto, being sized to be received between adjacent teeth without traversing any contact areas between the adjacent teeth from at least the front of the mouth;

said side flossing filaments being attached at spaced apart locations along said central member intermediate portion to be at a position to contact at least one of the adjacent teeth when said central member intermediate portion is received between the adjacent teeth;

said side filament intermediate portions being sufficiently flexible to effect a flossing action against the one of the adjacent teeth contacted by imparting a flossing motion to said side flossing filament;

a motive source; and a coupling connecting said motive source to said central member filament to impart said flossing motion to said side flossing filaments.

37. The apparatus of claim 36 wherein at least said central member intermediate portion, with said side flossing filaments attached thereto, are sized to be received in the sulcus between a tooth of the adjacent teeth and the adjacent inter-dental papilla portion of the gum for effecting said flossing action therein.

38. The apparatus of claim 36 wherein said coupling applies a moving force to said central member with at least one of a rotational and a translational component to move said central member and thereby impart said flossing motion to said side flossing filaments.

39. The apparatus of claim 36 wherein said motive source produces a rotational output drive and said coupling translates said rotational output drive into an oscillatory drive and supplies said oscillatory drive to said central member to produce said flossing motion of said side flossing filaments.

40. The apparatus of claim 36 wherein said motive source produces a rotational output drive and said coupling translates said rotational output drive into at least one of a rotational drive and a translational drive which is supplied to said central member to produce said flossing motion of said side flossing filaments.

41. The apparatus of claim 36 wherein said motive source is a motor producing a rotational output and said coupling converts said rotational output into a moving force applied to said central member which moves said central member along a path of travel substantially out of alignment with said central member when at rest to effect said flossing motion of said side flossing filaments.

42. The apparatus of claim 41 wherein said moving force applied to said central member rotates said central member as said central member is moved along said path of travel.

43. The apparatus of claim 36 wherein said motive source supplies a moving force and said coupling applies said moving force to said central member with a force component out of longitudinal alignment with said central member to effect said flossing motion of said side flossing filaments.

44. The apparatus of claim 36 wherein said motive source is rotatably connected by said coupling to said central member and rotates said central member about a driven longitudinal axis thereof.

45. The apparatus of claim 44 wherein said rotation of said central member is transmitted to said side flossing filaments to rotate said side flossing filaments about said central member longitudinal axis as said central member rotates thereabout with sufficient speed to whip against at least the one adjacent tooth.

46. The apparatus of claim 36 wherein at least one of said side flossing filaments has a sufficient length and is attached to said central member intermediate portion at a location to be positioned to engage a forward surface of the adjacent teeth, and wherein at least one of said side flossing filaments has a sufficient length and is attached to said central member intermediate portion at a location to be positioned to engage a rearward surface of the adjacent teeth when said central member intermediate portion is received between the adjacent teeth.

47. The apparatus of claim 36 wherein said central member intermediate portion has a maximum average transverse dimension of between 0.012 to 0.030 inches.

48. The apparatus of claim 36 wherein said side filament intermediate portions have a maximum average transverse dimension of between 0.002 to 0.008 inches.

49. The apparatus of claim 36 wherein said central member intermediate portion has a transverse dimension greater than an average transverse dimension of said side filament intermediate portions.

50. The apparatus of claim 49 wherein said side filament free-end portions have a transverse dimension greater than an average transverse dimension of said side filament intermediate portions.

51. The apparatus of claim 36 wherein said side filament free-end portions have a maximum average transverse dimension of between 0.004 to 0.010 inches.

52. The apparatus of claim 36 wherein said side filament free-end portions are weighted.

53. The apparatus of claim 36 wherein said side flossing filament have an average length of between 0.020 to 0.065 inches.

54. The apparatus of claim 36 wherein said side flossing filaments have unequal lengths.

55. The apparatus of claim 36 wherein said side flossing filaments have non-uniform lengths varying according to a longitudinal location of said side flossing filament along said central member intermediate portion with at least one of said side flossing filaments having a sufficient length and being attached to said central member intermediate portion at a first location to be positioned to engage a forward surface of the adjacent teeth, and at least one of said side flossing filaments having a sufficient length and being attached to said central member intermediate portion at a second location to be positioned to engage a rearward surface of the adjacent teeth when said central member intermediate portion is received between the adjacent teeth, and said side flossing filaments attached to said central member intermediate portion at locations between said first and second locations having a length less than said side flossing filaments at said first and second locations.

56. The apparatus of claim 55 wherein said side flossing filament at said first and second locations have a length of greater than 0.020 inches.

57. The apparatus of claim 55 wherein said side flossing filament at said first and second locations have a length of between 0.045 to 0.065 inches.

58. The apparatus of claim 36 wherein said side flossing filament are spaced apart along said central member intermediate portion by between 0.030 to 0.050 inches.

59. The apparatus of claim 36 wherein said side filament intermediate portions are sufficiently flexible to freely bend toward said central member intermediate portion during insertion thereof between the adjacent teeth.

60. The apparatus of claim 36 wherein said side filament intermediate portions are sufficiently flexible to be unable to fully support their own weight without substantial bending.

61. The apparatus of claim 36 wherein said side filament intermediate portions have a greater flexibility than said central member intermediate portion.

62. The apparatus of claim 61 wherein said central member intermediate portion has a greater resiliency than said side filament intermediate portions.

63. The apparatus of claim 36 wherein said central member intermediate portion has a greater resiliency than said side filament intermediate portions.

64. The apparatus of claim 36 wherein said side flossing filaments are non-abrasive.

65. The apparatus of claim 36 wherein said side flossing filaments are arranged along said central member intermediate portion in pairs.

66. The apparatus of claim 65 wherein said side flossing filaments of said pairs extend outward from said central member intermediate portion in different directions.

67. The apparatus of claim 66 wherein said side flossing filaments of said pairs extend outward from said central member intermediate portion in opposing directions.

68. The apparatus of claim 36 wherein said side flossing filaments extend transversely outward from said central member intermediate portion.

69. A flossing member for cleaning the surfaces of teeth in a human mouth, comprising:

a flexible, resilient central flossing filament including a base portion, a free-end portion, and an elongated intermediate portion located between said central filament base portion and said central filament free-end portion;

a plurality of flexible side flossing filaments, each having an attachment end portion attached to said central filament intermediate portion, a free-end portion and an elongated intermediate portion located between said side filament attachment portion and said side filament free-end portion;

said central filament intermediate and free-end portions, with said side flossing filaments attached thereto, being sized to be received between adjacent teeth without traversing any contact areas between the adjacent teeth from at least the front of the mouth, said central filament intermediate portion being sufficiently flexible and resilient to effect a first flossing action between the adjacent teeth by imparting a first flossing motion to said central filament intermediate portion;

said side flossing filaments being attached at spaced apart locations along said central filament intermediate portion to be at a position to contact at least one of the adjacent teeth when said central filament intermediate portion is received between the adjacent teeth; and said side filament intermediate portions being sufficiently flexible to effect a second flossing action by imparting a second flossing motion to said side flossing filament.

70. The flossing member of claim 69 wherein at least said central filament intermediate portion, with said side flossing filaments attached thereto, are sized to be received in the sulcus between a tooth of the adjacent teeth and the adjacent inter-dental papilla portion of the gum for effecting said first and second flossing actions therein.

71. The flossing member of claim 69 wherein said side flossing filaments are each attached to said central filament intermediate portion to be at one of a position between the adjacent teeth and a position adjacent to at least one of a forward surface and a rearward surface of the adjacent teeth when said central filament intermediate portion is received between the adjacent teeth to effect said second flossing action between the adjacent teeth and at one of said forward surface and said rearward surface of the adjacent teeth.

72. The flossing member of claim 69 wherein at least one of said side flossing filaments has a sufficient length and is attached to said central filament intermediate portion at a location to be positioned to engage a forward surface of the adjacent teeth, and wherein at least one of said side flossing filaments has a sufficient length and is attached to said central filament intermediate portion at a location to be positioned to engage a rearward surface of the adjacent teeth when said central filament intermediate portion is received between the adjacent teeth.

73. The flossing member of claim 69 wherein said central filament intermediate portion has a maximum average transverse dimension of between 0.012 to 0.030 inches.

74. The flossing member of claim 69 wherein said central filament intermediate portion has a maximum average transverse dimension of no greater than 0.030 inches.

75. The flossing member of claim 69 wherein said central filament intermediate portion has a generally circular cross-section with a diameter no greater than 0.030 inches.

76. The flossing member of claim 69 wherein said side filament intermediate portions have a maximum average transverse dimension of between 0.002 to 0.008 inches.

77. The flossing member of claim 69 wherein said side filament intermediate portions have a maximum average transverse dimension of no greater than 0.008 inches.

78. The flossing member of claim 69 wherein said side filament intermediate portions have a generally circular cross-section with a diameter no greater than 0.008 inches.

79. The flossing member of claim 69 wherein said central filament intermediate portion has a transverse dimension greater than an average transverse dimension of said side filament intermediate portions.

80. The flossing member of claim 79 wherein said side filament free-end portions have a transverse dimension greater than an average transverse dimension of said side filament intermediate portions.

81. The flossing member of claim 69 wherein said side filament free-end portions have a maximum average transverse dimension of between 0.004 to 0.010 inches.

82. The flossing member of claim 69 wherein said side filament free-end portions have a transverse dimension greater than an average transverse dimension of said side filament intermediate portions to provide an enlarged, weighted end for said side flossing filaments.

83. The flossing member of claim 69 wherein said side filament free-end portions have a generally circular cross-section.

84. The flossing member of claim 69 wherein said side filament free-end portions have a generally circular cross-section with a diameter of between 0.004 to 0.010 inches.

85. The flossing member of claim 69 wherein said side flossing filament have an average length of between 0.020 to 0.065 inches.

86. The flossing member of claim 69 wherein said side flossing filaments have unequal lengths.

87. The flossing member of claim 69 wherein said side flossing filaments have non-uniform lengths varying according to a longitudinal location of said side flossing filament along said central filament intermediate portion with at least one of said side flossing filaments having a sufficient length and being attached to said central filament intermediate portion at a first location to be positioned to engage a forward surface of the adjacent teeth, and at least one of said side flossing filaments having a sufficient length and being attached to said central filament intermediate portion at a second location to be positioned to engage a rearward surface of the adjacent teeth when said central filament intermediate portion is received between the adjacent teeth, and said side flossing filaments attached to said central filament intermediate portion at locations between said first and second locations having a length less than said side flossing filaments at said first and second locations.

88. The flossing member of claim 87 wherein said side flossing filament at said first and second locations have a length of greater than 0.020 inches.

89. The flossing member of claim 87 wherein said side flossing filament at said first and second locations have a length of between 0.045 to 0.065 inches.

90. The flossing member of claim 69 wherein said side flossing filament are spaced apart along said central filament intermediate portion by between 0.030 to 0.050 inches.

91. The flossing member of claim 69 wherein said side filament intermediate portions are sufficiently flexible to freely bend toward said central filament intermediate portion during insertion thereof between the adjacent teeth.

92. The flossing member of claim 69 wherein said side filament intermediate portions are sufficiently flexible to be unable to fully support their own weight without substantial bending.

93. The flossing member of claim 69 wherein said side filament intermediate portions are limp.

94. The flossing member of claim 69 wherein said side filament intermediate portions have a greater flexibility than said central filament intermediate portion.

95. The flossing member of claim 94 wherein said central filament intermediate portion has a greater resiliency than said side filament intermediate portions.

96. The flossing member of claim 69 wherein said central filament intermediate portion has a greater resiliency than said side filament intermediate portions.

97. The flossing member of claim 69 wherein said side flossing filaments are non-abrasive.

98. The flossing member of claim 97 wherein said central flossing filament is non-abrasive.

99. The flossing member of claim 69 wherein said side flossing filaments are arranged along said central filament intermediate portion in pairs.

100. The flossing member of claim 99 wherein said side flossing filaments of said pairs extend outward from said central filament intermediate portion in different directions.

101. The flossing member of claim 100 wherein said side flossing filaments of said pairs extend outward from said central filament intermediate portion in opposing directions.

102. The flossing member of claim 100 wherein said side flossing filaments of said pairs extend outward from said central filament intermediate portion in transverse, opposing directions.

103. The flossing member of claim 69 wherein said side flossing filaments and said central filament are molded as an integral unit from a plastic.

104. A flossing member for cleaning the surfaces of teeth in a human mouth, comprising:

an elongated central member including a base portion, a free-end portion, and an elongated intermediate portion located between said central member base portion and said central member free-end portion;

a plurality of flexible side flossing filaments, each having an attachment end portion attached to said central member intermediate portion, a free-end portion and an elongated intermediate portion located between said side filament attachment portion and said side filament free-end portion;

said central member intermediate and free-end portions, with said side flossing filaments attached thereto, being sized to be received between adjacent teeth without traversing any contact areas between the adjacent teeth from at least the front of the mouth;

said side flossing filaments being attached at spaced apart locations along said central member intermediate portion to be at a position to contact at least one of the adjacent teeth when said central member intermediate portion is received between the adjacent teeth; and said side filament intermediate portions being sufficiently flexible to effect a flossing action against the one of the adjacent teeth contacted by imparting a flossing motion to said side flossing filament.

105. The flossing member of claim 104 wherein at least said central member intermediate portion, with said side flossing filaments attached thereto, are sized to be received in the sulcus between a tooth of the adjacent teeth and the adjacent inter-dental papilla portion of the gum for effecting said flossing action therein.

106. The flossing member of claim 104 wherein said side flossing filaments are sufficiently flexible to freely bend toward said central member intermediate portion during insertion thereof between the adjacent teeth.

107. A method for cleaning the surfaces of teeth in a human mouth, comprising:

providing a motive source;

providing a flexible, resilient central flossing filament including a base portion, a free-end portion, and an elongated intermediate portion located between said central filament base portion and said central filament free-end portion;

providing a plurality of flexible side flossing filaments, each having an attachment end portion attached to said central filament intermediate portion, a free-end portion and an elongated intermediate portion located between said side filament attachment portion and said side filament free-end portion, said central filament intermediate and free-end portions, with said side flossing filaments attached thereto, being sized to be received between adjacent teeth without traversing any contact areas between the adjacent teeth from at least the front of the mouth, said central filament intermediate portion being sufficiently flexible and resilient to effect a first flossing action between the adjacent teeth by imparting a first flossing motion to said central filament intermediate portion, said side flossing filaments being attached at spaced apart locations along said central filament intermediate portion to be at one of a position between and a position adjacent to the adjacent teeth when said central filament intermediate portion is received therebetween, said side filament intermediate portions being sufficiently flexible to effect a second flossing action by imparting a second flossing motion to said side flossing filament;

positioning said central filament intermediate and free-end portions, with said side flossing filaments attached thereto, between adjacent teeth without traversing any contact areas between the adjacent teeth from the front of the mouth;

positioning at least said central filament intermediate portion and at least one of said side flossing filaments in the sulcus between a tooth and the adjacent inter-dental papilla portion of the gum for effecting said first and second flossing actions therein; and driving said central flossing filament and said side flossing filaments with said motive source to impart said first flossing motion to said central filament intermediate portion and said second flossing motion to said side flossing filaments.

108. The method of claim 107 wherein said side flossing filaments are sufficiently flexible to bend back against said central filament intermediate portion upon insertion between the adjacent teeth, and said step of positioning at least said central filament intermediate portion and at least one of said side flossing filaments in the sulcus includes bending said at least one side flossing filament back against said central filament intermediate portion upon insertion between the tooth and the adjacent inter-dental papilla portion of the gum.

109. The method of claim 107 wherein said step of driving of said central flossing filament and said side flossing filaments includes applying a moving force to said central flossing filament with at least one of a rotational and a translational component to impart said first flossing motion to said central filament intermediate portion and said second flossing motion to said side flossing filaments.

110. The method of claim 107 wherein said step of driving of said central flossing filament and said side flossing filaments includes applying a rotational drive to said central flossing filament at a sufficient rotational speed to produce centrifugal force on said side flossing filaments attached thereto sufficient to extend said side flossing filaments substantially radially outward.

111. The method of claim 107 wherein said step of driving of said central flossing filament and said side flossing filaments includes applying an oscillatory drive to said central flossing filament at a sufficient translatory speed to cause said side flossing filaments attached thereto to whip about.

112. The method of claim 107 wherein said step of driving of said central flossing filament and said side flossing filaments includes applying a rotational moving force to said central flossing filament which moves said central flossing filament along a path of travel substantially out of alignment with said central flossing filament when at rest to effect said first flossing motion of said central filament intermediate portion and rotate said side flossing filaments to effect said second flossing motion of said side flossing filaments.

113. An adapter usable to convert a teeth cleaning device having an electric motor positioned within a case with a rotational output drive shaft positioned toward an open end of the case for use with an improved flossing member, comprising:

a drive coupler having a shaft engagement portion attachable to the output shaft of the motor, and a flossing member attachment portion;

a coupler support having a case attachment portion configured for removable attachment to the case at the open end thereof, and a coupler support portion supporting said flossing member attachment portion of said drive coupler; and a flossing member including a flexible, resilient central flossing filament and a plurality of flexible side flossing filaments, said central flossing filament having a base portion, a free-end portion, and an elongated intermediate portion located between said central filament base portion and said central filament free-end portion, said central filament base portion being configured for releasable connection to said flossing member attachment portion of said drive coupler to transmit the rotational output drive of the motor thereto, each of said side flossing filaments having an attachment end portion attached to said central filament intermediate portion, a free-end portion and an elongated intermediate portion located between said side filament attachment portion and said side filament free-end portion, said central filament intermediate and free-end portions, with said side flossing filaments attached thereto, being sized to be received between adjacent teeth without traversing any contact areas between the adjacent teeth from at least the front of the mouth, said central filament intermediate portion being sufficiently flexible and resilient to effect a first flossing action between the adjacent teeth by imparting a first flossing motion to said central filament intermediate portion, said side flossing filaments being attached at spaced apart locations along said central filament intermediate portion to be at one of a position between the adjacent teeth and a position adjacent to at least one of a forward surface and a rearward surface of the adjacent teeth when said central filament intermediate portion is received between the adjacent teeth, said side filament intermediate portions being sufficiently flexible to effect a second flossing action against the tooth contacted by imparting a second flossing motion to said side flossing filament.

114. The adapter of claim 113 wherein said drive coupler includes a drive cable attached between said shaft engagement portion and said flossing member attachment portion, said coupler support portion rotatably supporting said flossing member attachment portion to permit rotation thereof by said drive cable in response to a rotational drive output of the output shaft of the motor.

115. The adapter of claim 114 wherein said flossing member attachment portion has a generally spherical shape and said coupler support portion includes a generally spherical shaped socket within which said spherical flossing member attachment portion is rotatably positioned.

116. The adapter of claim 114 wherein said flossing member attachment portion has a socket configured to releasably retain therein said central filament base portion.

117. An apparatus for cleaning the surfaces of teeth in a human mouth, comprising:

an elongated central member including a base portion, a free-end portion, and an elongated intermediate portion located between said central member base portion and said central member free-end portion;

a plurality of flexible side flossing filaments, each having an attachment end portion attached to said central member intermediate portion, a free-end portion and an elongated intermediate portion located between said side filament attachment portion and said side filament free-end portion;

said central member intermediate and free-end portions, with said side flossing filaments attached thereto, being sized to be received between adjacent teeth without traversing any contact areas between the adjacent teeth from at least the front of the mouth;

said side flossing filaments being attached at spaced apart locations along said central member intermediate portion to be at a position to contact at least one of the adjacent teeth when said central member intermediate portion is received between the adjacent teeth;

said side filament intermediate portions being sufficiently flexible to effect a flossing action against the one of the adjacent teeth contacted by imparting a flossing motion to said side flossing filament;

a handle; and a coupling releasably connecting said central member filament to said handle.

118. The apparatus of claim 117 wherein at least said central member intermediate portion, with said side flossing filaments attached thereto, are sized to be received in the sulcus between a tooth of the adjacent teeth and the adjacent inter-dental papilla portion of the gum for effecting said flossing action therein.

119. The apparatus of claim 117 wherein said side flossing filaments are sufficiently flexible to bend back against said central member intermediate portion upon insertion between the adjacent teeth, and at least said central member intermediate portion, with said side flossing filaments attached thereto and bent back there against, are sized to be received in the sulcus between a tooth of the adjacent teeth and the adjacent inter-dental papilla portion of the gum for effecting said first and second flossing actions therein.

120. The apparatus of claim 117 wherein said coupling applies a moving force to said central member with at least one of a rotational and a translational component to move said central member and impart said flossing motion to said side flossing filament.

121. The apparatus of claim 117 wherein said central member is a flexible, resilient flossing filament.

122. The apparatus of claim 36 wherein said coupling includes a flossing member attachment portion with a socket configured to releasably retain therein said central member base portion, said flossing member attachment portion moving said central member to impart said flossing motion to said side flossing filaments.

* * * * *